US008183002B2

(12) United States Patent
Adamczyk et al.

(10) Patent No.: US 8,183,002 B2
(45) Date of Patent: May 22, 2012

(54) AUTOANTIBODY ENHANCED IMMUNOASSAYS AND KITS

(75) Inventors: Maciej Adamczyk, Gurnee, IL (US); Jeffrey R. Brashear, Mundelein, IL (US); Phillip G. Mattingly, Third Lake, IL (US)

(73) Assignee: Abbott Laboratories, Abbott Park, IL (US)

( * ) Notice: Subject to any disclaimer, the term of this patent is extended or adjusted under 35 U.S.C. 154(b) by 351 days.

(21) Appl. No.: 12/630,697

(22) Filed: Dec. 3, 2009

(65) Prior Publication Data
US 2011/0136103 A1    Jun. 9, 2011

(51) Int. Cl.
*G01N 33/53*    (2006.01)
*G01N 31/00*    (2006.01)
(52) U.S. Cl. ......... 435/7.21; 435/4; 435/7.1; 435/287.9; 436/501; 436/518; 436/525; 436/529; 436/535; 436/809; 427/287; 427/337; 427/338; 530/300; 530/350
(58) Field of Classification Search .................. None
See application file for complete search history.

(56) References Cited

U.S. PATENT DOCUMENTS

| | | | |
|---|---|---|---|
| 3,817,837 | A | 6/1974 | Rubenstein et al. |
| 3,850,752 | A | 11/1974 | Schuurs et al. |
| 3,939,350 | A | 2/1976 | Kronick et al. |
| 3,996,345 | A | 12/1976 | Ullman et al. |
| 4,275,149 | A | 6/1981 | Litman et al. |
| 4,277,437 | A | 7/1981 | Maggio |
| 4,366,241 | A | 12/1982 | Tom et al. |
| 5,006,309 | A | 4/1991 | Khalil et al. |
| 5,063,081 | A | 11/1991 | Cozzette et al. |
| 5,089,424 | A | 2/1992 | Khalil et al. |
| 5,244,630 | A | 9/1993 | Khalil et al. |
| 5,468,646 | A | 11/1995 | Mattingly et al. |
| 5,543,524 | A | 8/1996 | Mattingly et al. |
| 5,783,699 | A | 7/1998 | Mattingly et al. |
| 6,670,115 | B1 | 12/2003 | Zhang |
| 6,682,648 | B1 | 1/2004 | MacPhee et al. |
| 6,887,714 | B2 | 5/2005 | Fritsch et al. |
| 7,045,310 | B2 | 5/2006 | Buck, Jr. et al. |
| 7,045,364 | B2 | 5/2006 | Limoges et al. |
| 2003/0170881 | A1 | 9/2003 | Davis et al. |
| 2004/0018577 | A1 | 1/2004 | Emerson Campbell et al. |
| 2005/0054078 | A1 | 3/2005 | Miller et al. |
| 2006/0160164 | A1 | 7/2006 | Miller et al. |

FOREIGN PATENT DOCUMENTS

| | | | |
|---|---|---|---|
| EP | 425633 | B1 | 7/1994 |
| EP | 273115 | B1 | 9/1994 |
| EP | 424634 | B1 | 6/1995 |
| EP | 406473 | B1 | 9/1995 |
| EP | 326100 | B1 | 9/1996 |

OTHER PUBLICATIONS

Adamczyk et al., "Linker-Medicated Modulation of the Cheiluminescent Signal From N10-(3-Sulfopropyl)-N-Sulfonylacridinium-9-carboxamide Tracers," Bioconjugate Chem, 2000, pp. 714-724, vol. 11.

Adamczyk et al., "Modulation of the Chemiluminescent Signal From N10-(3-Sulfopropyl)-N-Sulfonylacridinium-9-carboxamides," Tetrahedron, 1999, pp. 10899-10914, vol. 55.
Adamczyk et al., "Neopentyl 3-Triflyloxypropanesulfaonate Areactive Sulfopropylation Reagent for the Preparation of Chemiluminescent Labels," J Org Chem, 1998, pp. 5636-5639, vol. 63.
Adamczyk et al., "Regiodependent Luminescence Quenching of Biotinylated N-Sulfonyl-acridinium-9-carboxamides by Avidin," Organic Letters, 2003, pp. 3779-3782, vol. 5 (21).
Adamczyk et al., "Synthesis of a Chemiluminescent Acridinium Hydroxylamine (AHA) for the Direct Detection of Abasic Sites in DNA," Organic Letters, 1999, pp. 779-781, vol. 1 (5).
Akerstrom et al., "Protein G: A Powerful Tool for Binding and Detection of Monoclonal and Polyclonal Antibodies," Immunology, 1985, vol. 135 (4) pp. 2589-2592.
Clackson T., et al., "Making antibody fragments using phage display libraries," Nature,, 1991, 352, 624-628.
Coligan, et al., Current Protocols in Protein Science, TOC, U.S. Appl. No. 12/443,492, filled on Oct. 12, 2007.
Co-pending U.S. Appl. No. 06/921,979.
Co-pending U.S. Appl. No. 07/150,278.
Co-pending U.S. Appl. No. 07/375,029.
Daniel P. Stites, et al, "Basic and Clinical Immunology" LANGE medical book, 1991.
David J. Asai, et al, "Methods in Cell Biology" Antibodies in Cell Biology, vol. 37, 1993.
Goran Kronvall, et al, "A Surface Component in Group A, C, and G *Streptococci* With Non-Immune Reactivity for Immunoglobulin G" Boilinology, vol. 111 (5), 1973.
Griffiths A. D., et al., "Human anti-self antibodies with high specificity from phage display libraries," The EMBO J, 1993, 12 (2), 725-734.
Hoogenboom H. R., et al., Multi-subunit proteins on the surface of filamentous phage: methodologies for displaying antibody (Fab) heavy and light chains, Nucleic Acids Research, 1991, 19 (15), Oxford University Press, 4133-4137.
Kohler G., et al., "Continuous cultures of fused cells secreting antibody of predefined specificity," Nature , 1975, 256 (5517), 495-497.
Langone, et al, "Production of Antisera with Small Doses of Immunogen: Multiple Intradermal Injections", MethodsEnzymology, vol. 73, 46-52, 1981.
Marks, J. D. et al., "By-passing immunization. Human antibodies from V-gene libraries displayed on phage," J Mol Biol, 1991, vol. 222, pp. 581-597.
Marks, J.D. et al. (1992). "By-Passing Immunization: Building High Affinity Human Antibodies by Chain Shuffling," Bio/Technol. 10:779:783. cited by other.
Mattingly et al., "Chemiluminescent N-Sulfonylacridinium-9-Carboxamides and Their Application in Clinical Assays," Luminescence Biotechnology: Instruments and Applications (CRC Press: Boca Raton 2000), 2002, pp. 77-105.
Mattingly Phillip G., "Chemiluminescent 10-Methyl-Acridinium-9(N-Sulphonylcarboxamide) Salts. Synthesis and Kinetics of Light Emission," Journal of Bioluminescence and Chemiluminescence, 1991, pp. 107-114, vol. 6.

(Continued)

*Primary Examiner* — Lisa Cook
(74) *Attorney, Agent, or Firm* — Cheryl L. Becker

(57) ABSTRACT

The present disclosure provides immunoassays and kits for detection or quantification of an analyte of interest in a test sample that potentially contains endogenously produced autoantibodies reactive with the analyte.

19 Claims, 4 Drawing Sheets

OTHER PUBLICATIONS

McCafferty J., et al., "Phage antibodies: filamentous phage displaying antibody variable domains," Nature, 1990, 348, 552-554.

McCapra, et al., "Chemiluminescence Involving Peroxide Decompositions", Photochemistry and Photobiology, 1965, 4, 1111-1121.

Razavi, "Stable and versatile active acridinium esters I," Luminescence, 2000, pp. 239-244, vol. 15.

Razavi, "Stable and versatile active acridinium esters II," Luminescence, 2000, pp. 245-249, vol. 15.

U.S. Appl. No. 11/588,073, filed Oct. 26, 2006.

AUTOANTIBODY ENHANCED IMMUNOASSAYS AND KITS

RELATED APPLICATION INFORMATION

None.

TECHNICAL FIELD

The present disclosure relates to immunoassays and kits for detecting an analyte of interest in a test sample, and in particular to methods and kits for detecting an analyte in a human test sample that may contain endogenous anti-analyte antibodies.

BACKGROUND

Immunoassay techniques have been known for the last few decades and are now commonly used in medicine for a wide variety of diagnostic purposes to detect target analytes in a biological sample. Immunoassays exploit the highly specific binding of an antibody to its corresponding antigen, wherein the antigen is the target analyte. Typically, quantification of either the antibody or antigen is achieved through some form of labeling such as radio- or fluorescence-labeling. Sandwich immunoassays involve binding the target analyte in the sample to the antibody site (which is frequently bound to a solid support), binding labeled antibody to the captured analyte, and then measuring the amount of bound labeled antibody, wherein the label generates a signal proportional to the concentration of the target analyte inasmuch as labeled antibody does not bind unless the analyte is present in the sample.

A problem with this general approach is that many patients have circulating endogenous antibodies, or "autoantibodies" against an analyte of clinical interest. For example, autoantibodies have been described for cardiac troponin, myeloperoxidase (MPO), prostate specific antigen (PSA), and thyroid stimulating hormone (TSH), and other clinically significant analytes. Autoantibodies create interference in typical sandwich immunoassays that are composed of two or more analyte-specific antibodies. For example, cardiac troponin-reactive autoantibodies may interfere with the measurement of cTnI using conventional midfragment-specific immunoassays. Thus, interference from autoantibodies can produce erroneous results, particularly near the cut-off values established for clinical diagnoses, and increases the risk of false negative diagnostic results and the risk that individuals will not obtain a timely diagnosis.

One approach to addressing this problem is to choose analyte-specific antibodies that bind to specific epitopes distinct from the analyte epitopes that react with the autoantibodies. Following this general approach, efforts have focused on exploring the use of thousands of different combinations of two, three and even four analyte-specific antibodies to avoid interference from autoantibodies. However, this effort has been largely unsuccessful. It is now evident that autoantibodies against complex protein analytes are likely to be polyclonal within a particular sample, and may be even more diverse among samples from different individuals. Interference from diverse polyclonal autoantibodies may explain the observation that as little as 25% or even less of an analyte protein sequence binds to analyte-specific antibodies, which may in turn explain the lack of success using this approach.

A need exists in the art for new immunoassay methods that compensate for interference by autoantibodies in a sample, and in particular for such methods that do so without involving redesign of the analyte detection or capture antibodies.

SUMMARY

In one aspect, the present disclosure relates to an immunoassay for detecting an analyte of interest in a test sample, the immunoassay comprising the steps of:

(a) contacting a test sample suspected of containing an analyte of interest with a first antibody that binds to at least one epitope on the analyte of interest to form a first antibody-analyte complex, wherein the first antibody is immobilized on a solid phase, and further wherein at least one autoantibody in the test sample binds to at least one epitope on the analyte of interest to form an autoantibody-analyte complex, wherein said autoantibody binds to the solid phase;

(b) contacting said mixture comprising a first antibody-analyte complex and an autoantibody-analyte complex with a second antibody to form a measurable assembly comprising a first antibody-analyte-second antibody complex and an autoantibody-analyte-second antibody complex; wherein the second antibody binds to at least one epitope on the analyte of interest, and further wherein, an optical, electrical, or change-of-state signal of the assembly is measured.

In the above immunoassay, the second antibody can be conjugated to a detectable label, wherein the detectable label is an enzyme, oligonucleotide, nanoparticle chemiluminophore, fluorophore, fluorescence quencher, chemiluminescence quencher, or biotin.

In the above immunoassay, an optical signal can be measured as an analyte concentration-dependent change in chemiluminescence, fluorescence, phosphorescence, electrochemiluminescence, ultraviolet absorption, visible absorption, infrared absorption, refraction, surface plasmon resonance.

In the above immunoassay, the electrical signal can be measured as an analyte concentration dependent change in current, resistance, potential, mass to charge ratio, or ion count.

In the above immunoassay, the change-of-state signal can be measured as an analyte concentration dependent change in size, solubility, mass, or resonance.

In another aspect, the present disclosure relates to an immunoassay for detecting an analyte of interest in a test sample, the immunoassay comprising the steps of:

(a) contacting a test sample suspected of containing an analyte of interest with a first antibody that binds to at least one epitope on the analyte of interest to form a first antibody-analyte complex, wherein the first antibody is immobilized on a solid phase, and further wherein at least one autoantibody in the test sample binds to at least one epitope on the analyte of interest to form an autoantibody-analyte complex, wherein said autoantibody binds to the solid phase;

(b) contacting said mixture comprising a first antibody-analyte complex and an autoantibody-analyte complex, with a second antibody that has been conjugated to a detectable label to form a first antibody-analyte-second antibody complex and an autoantibody-analyte-second antibody complex; wherein the second antibody binds to at least one epitope on the analyte of interest and further wherein, the detectable label is at least one acridinium compound;

(c) generating or providing a source of hydrogen peroxide to the mixture of step (b);

(d) adding a basic solution to the mixture of step (c) to generate a light signal; and (e) measuring the light signal generated by or emitted in step (d) and detecting the analyte of interest in the test sample.

In the above immunoassay, the analyte of interest can be a cardiac troponin, thyroid stimulating hormone (TSH), beta human chorionic gonadotropin (beta-HCG); myeloperoxidase (MPO), prostate specific antigen (PSA), human B-type natriuretic peptide (BNP), myosin light chain 2, myosin-6 or myosin-7.

In the above immunoassay, the test sample can be whole blood, serum, or plasma.

In the above immunoassay, any acridinium compound can be used. For example, the acridinium compound can be an acridinium-9-carboxamide having a structure according to formula I:

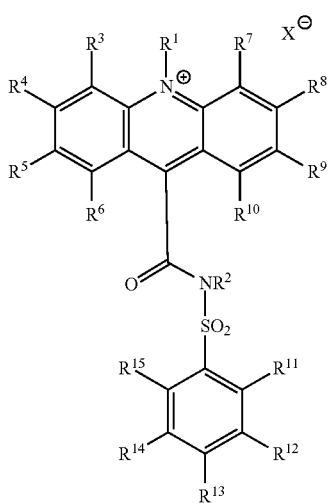

I wherein R1 and R2 are each independently selected from the group consisting of: alkyl, alkenyl, alkynyl, aryl or aralkyl, sulfoalkyl, carboxyalkyl and oxoalkyl, and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\ominus}$ is an anion.

Alternatively, the acridinium compound is an acridinium-9-carboxylate aryl ester having a structure according to formula II:

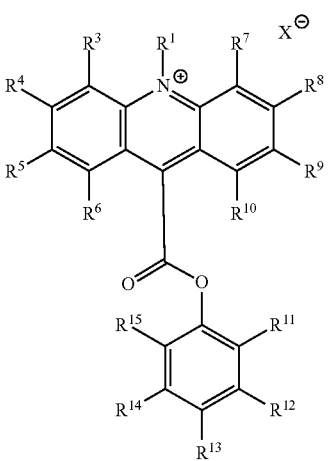

II wherein R1 is an alkyl, alkenyl, alkynyl, aryl or aralkyl, sulfoalkyl, carboxyalkyl and oxoalkyl; and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\ominus}$ is an anion.

In the above immunoassay, the solid phase can be selected from the group consisting of a magnetic particle, bead, test tube, microtiter plate, cuvette, membrane, a scaffolding molecule, quartz crystal, film, filter paper, disc and chip.

In the above immunoassay, the first antibody can be selected from the group consisting of a polyclonal antibody, a monoclonal antibody, a chimeric antibody, a human antibody, and an affinity maturated antibody.

In the above immunoassay the second antibody can be selected from the group consisting of a polyclonal antibody, a monoclonal antibody, a chimeric antibody, a human antibody, and an affinity maturated antibody.

In the above immunoassay the hydrogen peroxide can be provided by adding a buffer or a solution containing hydrogen peroxide.

In the above immunoassay, the hydrogen peroxide can be generated by adding a hydrogen peroxide generating enzyme to the test sample. The hydrogen peroxide generating enzyme can be selected for example from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, arylaldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinylalcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

In the above immunoassay, the basic solution can be a solution having a pH of at least about 10.

Optionally, the above immunoassay may further comprise the step of quantifying the amount of the analyte of interest in the test sample by relating the amount of light signal in step (e) to the amount of the analyte of interest in the test sample either by use of a standard curve for the analyte of interest or by comparison to a reference standard. The immunoassay may be adapted for use in an automated system or semi-automated system.

In another aspect, the present disclosure relates to a kit for detecting or quantifying an analyte of interest in a test sample, the kit comprising a solid phase capable of binding autoantibodies present in the test sample; a first antibody that binds to at least one epitope on the analyte of interest, the first antibody bound to the solid phase; a second antibody that binds to at least one epitope on the analyte of interest; and instructions for detecting or quantifying the analyte of interest.

In the above kit, a detectable label can be conjugated to the second antibody. The detectable label can be an enzyme, oligonucleotide, nanoparticle chemiluminophore, fluorophore, fluorescence quencher, chemiluminescence quencher, or biotin. In certain embodiments, the detectable label is an acridinium compound. The acridinium compound can be an acridinium-9-carboxamide having a structure according to formula I:

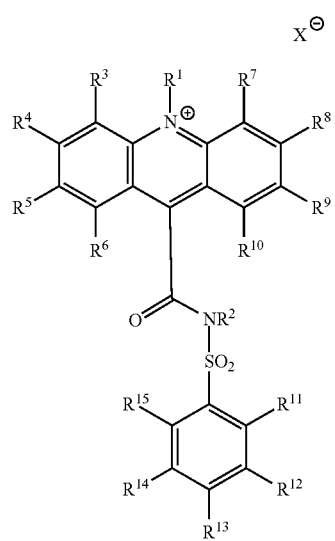

I wherein R1 and R2 are each independently selected from the group consisting of: alkyl, alkenyl, alkynyl, aryl or aralkyl, sulfoalkyl, carboxyalkyl and oxoalkyl, and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion. Alternatively, the acridinium compound can be an acridinium-9-carboxylate aryl ester having a structure according to formula II:

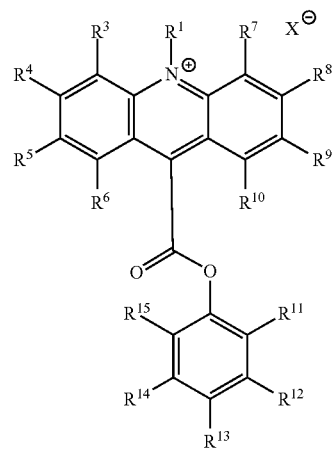

II wherein R1 is an alkyl, alkenyl, alkynyl, aryl or aralkyl, sulfoalkyl, carboxyalkyl and oxoalkyl; and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion. The above kit can further include a basic solution, such as a solution having a pH of at least about 10.

The above kit may further include a hydrogen peroxide source, which can be a buffer, a solution containing hydrogen peroxide, or a hydrogen peroxide generating enzyme. In kits containing a hydrogen peroxide generating enzyme, the enzyme can be selected from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate)oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

In the above it, the solid phase can be selected from the group consisting of a magnetic particle, a bead, a test tube, a microtiter plate, a cuvette, a membrane, a scaffolding molecule, a quartz crystal, a film, a filter paper, a disc and a chip.

In the above it, the first antibody and the second antibody can each bind to an epitope on an analyte of interest selected from the group consisting of cardiac troponin, thyroid stimulating hormone (TSH), beta human chorionic gonadotropin (beta-HCG); myeloperoxidase (MPO), prostate specific antigen (PSA), human B-type natriuretic peptide (BNP), myosin light chain 2, myosin-6 and myosin-7.

In another aspect, the present disclosure relates to an immunodetection composition including a first detection complex comprising a first antibody reactive with an analyte of interest and bound to a solid phase, the analyte of interest, and a second antibody reactive with the analyte of interest, wherein the second antibody has a detectable label, and a second detection complex comprising an autoantibody reactive with the analyte of interest and bound to the solid phase, the analyte of interest, and the second antibody, wherein the first and second complexes generate a measurable optical, electrical, or change-of-state signal from the detectable label. In the above immunodetection composition, the first detection complex can be bound to the second detection complex on the solid phase.

DETAILED DESCRIPTION

Figure 1:
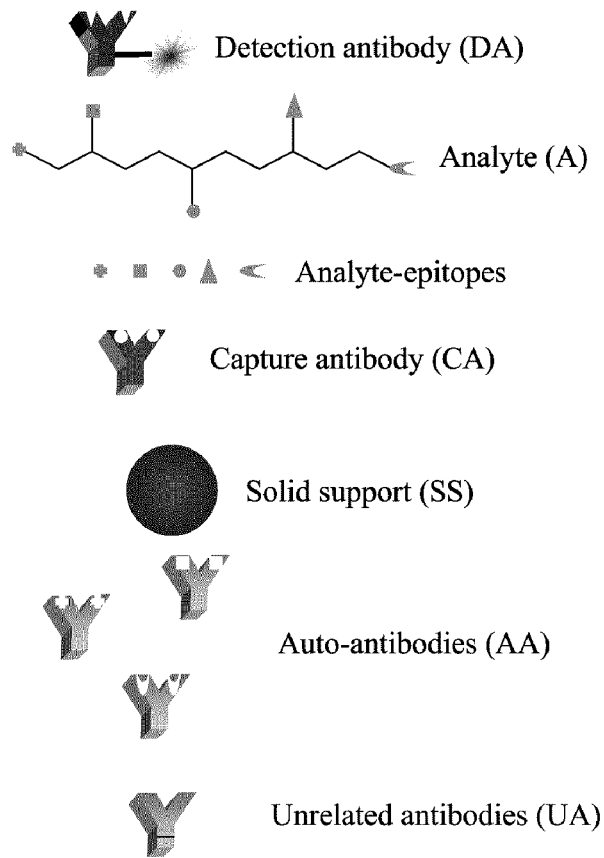
FIG. 1 shows a schematic diagram of a typical immunoassay reaction sequence.
Figure 1:
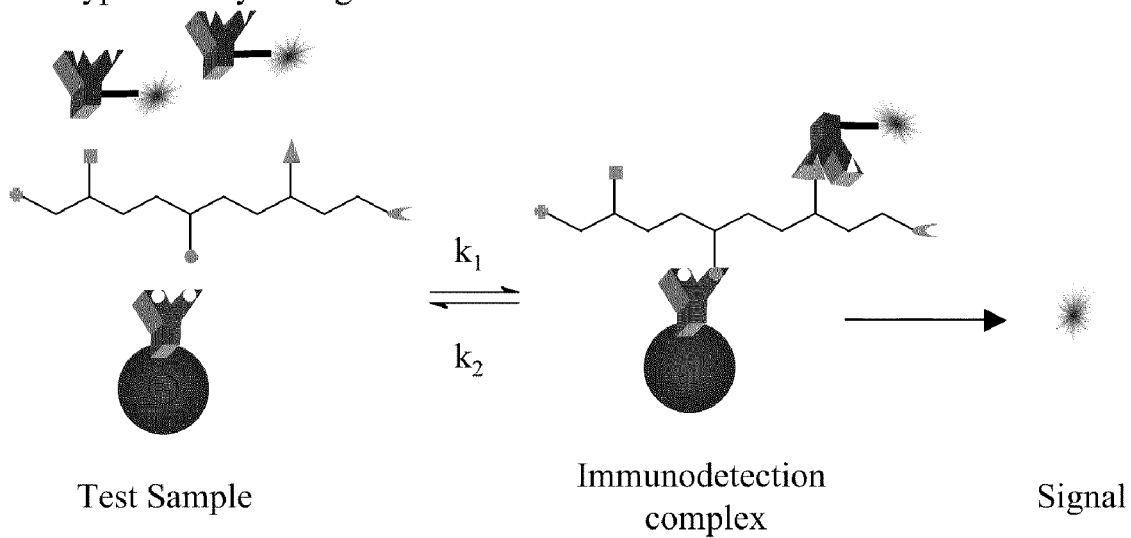

The present disclosure relates to immunoassay methods and kits for detecting an analyte of interest in a test sample, and more particularly to methods and kits for detecting an analyte in a human test sample that may contain endogenous anti-analyte antibodies. Specifically, the inventors have discovered an alternative approach to address the problem of autoantibodies in immunoassay detection of clinically significant analytes in a sample, in which a solid phase that bears an analyte-specific antibody is also capable of binding autoantibodies against the analyte that may be present in the sample. This assay approach compensates for the presence of autoantibodies in the sample without redesign of the analyte-specific detection antibodies or the capture antibodies, does not require use of an extra anti-human IgG detection conjugate, and avoids the need of a second assay to identify problematic samples.

A. DEFINITIONS

Section headings as used in this section and the entire disclosure herein are not intended to be limiting.

As used herein, the singular forms "a," "an" and "the" include plural referents unless the context clearly dictates otherwise. For the recitation of numeric ranges herein, each intervening number there between with the same degree of precision is explicitly contemplated. For example, for the range 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9 and 7.0 are explicitly contemplated.

a) Acyl (and Other Chemical Structural Group Definitions)

As used herein, the term "acyl" refers to a —C(O)$R_a$ group where $R_a$ is hydrogen, alkyl, cycloalkyl, cycloalkylalkyl, phenyl or phenylalkyl. Representative examples of acyl include, but are not limited to, formyl, acetyl, cylcohexylcarbonyl, cyclohexylmethylcarbonyl, benzoyl, benzylcarbonyl and the like.

As used herein, the term "alkenyl" means a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

As used herein, the term "alkyl" means a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

As used herein, the term "alkyl radical" means any of a series of univalent groups of the general formula $C_nH_{2n+1}$ derived from straight or branched chain hydrocarbons.

As used herein, the term "alkoxy" means an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

As used herein, the term "alkynyl" means a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

As used herein, the term "amido" refers to an amino group attached to the parent molecular moiety through a carbonyl group (wherein the term "carbonyl group" refers to a —C(O)— group).

As used herein, the term "amino" means —N$R_bR_c$, wherein $R_b$ and $R_c$ are independently selected from the group consisting of hydrogen, alkyl and alkylcarbonyl.

As used herein, the term "aralkyl" means an aryl group appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

As used herein, the term "aryl" means a phenyl group, or a bicyclic or tricyclic fused ring system wherein one or more of the fused rings is a phenyl group. Bicyclic fused ring systems are exemplified by a phenyl group fused to a cycloalkenyl group, a cycloalkyl group, or another phenyl group. Tricyclic fused ring systems are exemplified by a bicyclic fused ring system fused to a cycloalkenyl group, a cycloalkyl group, as defined herein or another phenyl group. Representative examples of aryl include, but are not limited to, anthracenyl, azulenyl, fluorenyl, indanyl, indenyl, naphthyl, phenyl, and tetrahydronaphthyl. The aryl groups of the present disclosure can be optionally substituted with one-, two, three, four, or five substituents independently selected from the group consisting of alkoxy, alkyl, carboxyl, halo, and hydroxyl.

As used herein, the term "carboxy" or "carboxyl" refers to —$CO_2H$ or —$CO_2^-$.

As used herein, the term "carboxyalkyl" refers to a —$(CH_2)_nCO_2H$ or —$(CH_2)_nCO_2^-$ group where n is from 1 to 10.

As used herein, the term "cyano" means a —CN group.

As used herein, the term "cycloalkenyl" refers to a non-aromatic cyclic or bicyclic ring system having from three to ten carbon atoms and one to three rings, wherein each five-membered ring has one double bond, each six-membered ring has one or two double bonds, each seven- and eight-membered ring has one to three double bonds, and each nine- to ten-membered ring has one to four double bonds. Representative examples of cycloalkenyl groups include cyclohexenyl, octahydronaphthalenyl, norbornylenyl, and the like. The cycloalkenyl groups can be optionally substituted with one, two, three, four, or five substituents independently selected from the group consisting of alkoxy, alkyl, carboxyl, halo, and hydroxyl.

As used herein, the term "cycloalkyl" refers to a saturated monocyclic, bicyclic, or tricyclic hydrocarbon ring system having three to twelve carbon atoms. Representative examples of cycloalkyl groups include cyclopropyl, cyclopentyl, bicyclo[3.1.1]heptyl, adamantyl, and the like. The cycloalkyl groups of the present disclosure can be optionally substituted with one, two, three, four, or five substituents independently selected from the group consisting of alkoxy, alkyl, carboxyl, halo, and hydroxyl.

As used herein, the term "cycloalkylalkyl" means a —$R_dR_e$ group where $R_d$ is an alkylene group and $R_e$ is cycloalkyl group. A representative example of a cycloalkylalkyl group is cyclohexylmethyl and the like.

As used herein, the term "halogen" means a —Cl, —Br, —I or —F; the term "halide" means a binary compound, of which one part is a halogen atom and the other part is an element or radical that is less electronegative than the halogen, e.g., an alkyl radical.

As used herein, the term "hydroxyl" means an —OH group.

As used herein, the term "nitro" means a —$NO_2$ group.

As used herein, the term "oxoalkyl" refers to —$(CH_2)_nC(O)R_a$, where $R_a$ is hydrogen, alkyl, cycloalkyl, cycloalkylalkyl, phenyl or phenylalkyl and where n is from 1 to 10.

As used herein, the term "phenylalkyl" means an alkyl group which is substituted by a phenyl group.

As used herein, the term "sulfo" means a —$SO_3H$ group.

As used herein, the term "sulfoalkyl" refers to a —$(CH_2)_nSO_3H$ or —$(CH_2)_nSO_3^-$ group where n is from 1 to 10.

b) Anion

As used herein, the term "anion" refers to an anion of an inorganic or organic acid, such as, but not limited to, hydrochloric acid, hydrobromic acid, sulfuric acid, methane sulfonic acid, formic acid, acetic acid, oxalic acid, succinic acid, tartaric acid, mandelic acid, fumaric acid, lactic acid, citric acid, glutamic acid, aspartic acid, phosphate, trifluoromethansulfonic acid, trifluoroacetic acid and fluorosulfonic acid and any combinations thereof.

c) Antibody

As used herein, the term "antibody" refers to a protein consisting of one or more polypeptides substantially encoded by immunoglobulin genes or fragments of immunoglobulin genes, and encompasses polyclonal antibodies, monoclonal antibodies, and fragments thereof, as well as molecules engineered from immunoglobulin gene sequences. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

d) Hydrogen Peroxide Generating Enzyme

As used herein, the term "hydrogen peroxide generating enzyme" refers to an enzyme that is capable of producing as a reaction product the chemical compound having the molecular formula $H_2O_2$, i.e. hydrogen peroxide. Non-limiting examples of hydrogen peroxide generating enzymes are listed below in Table 1.

TABLE 1

| ACCEPTED COMMON NAME | IUBMB ENZYME NOMENCLATURE | PREFERRED SUBSTRATE |
| --- | --- | --- |
| (R)-6-hydroxynicotine oxidase | EC 1.5.3.6 | (R)-6-hydroxynicotine |
| (S)-2-hydroxy acid oxidase | EC 1.1.3.15 | S)-2-hydroxy acid |
| (S)-6-hydroxynicotine oxidase | EC 1.5.3.5 | (S)-6-hydroxynicotine |
| 3-aci-nitropropanoate oxidase | EC 1.7.3.5 | 3-aci-nitropropanoate |
| 3-hydroxyanthranilate oxidase | EC 1.10.3.5 | 3-hydroxyanthranilate |
| 4-hydroxymandelate oxidase | EC 1.1.3.19 | (S)-2-hydroxy-2-(4-hydroxyphenyl)acetate |
| 6-hydroxynicotinate dehydrogenase | EC 1.17.3.3 | 6-hydroxynicotinate |
| Abscisic-aldehyde oxidase | EC 1.2.3.14 | abscisic aldehyde |
| acyl-CoA oxidase | EC 1.3.3.6 | acyl-CoA |
| Alcohol oxidase | EC 1.1.3.13 | a primary alcohol |
| Aldehyde oxidase | EC 1.2.3.1 | an aldehyde |
| amine oxidase | | |
| amine oxidase (copper-containing) | EC 1.4.3.6 | primary monoamines, diamines and histamine |
| amine oxidase (flavin-containing) | EC 1.4.3.4 | a primary amine |
| aryl-alcohol oxidase | EC 1.1.3.7 | an aromatic primary alcohol (2-naphthyl)methanol 3-methoxybenzyl alcohol |
| aryl-aldehyde oxidase | EC 1.2.3.9 | an aromatic aldehyde |
| Catechol oxidase | EC 1.1.3.14 | Catechol |
| cholesterol oxidase | EC 1.1.3.6 | Cholesterol |
| Choline oxidase | EC 1.1.3.17 | Choline |
| columbamine oxidase | EC 1.21.3.2 | Columbamine |
| cyclohexylamine oxidase | EC 1.4.3.12 | Cyclohexylamine |
| cytochrome c oxidase | EC 1.9.3.1 | |
| D-amino-acid oxidase | EC 1.4.3.3 | a D-amino acid |
| D-arabinono-1,4-lactone oxidase | EC 1.1.3.37 | D-arabinono-1,4-lactone |
| D-arabinono-1,4-lactone oxidase | EC 1.1.3.37 | D-arabinono-1,4-lactone |
| D-aspartate oxidase | EC 1.4.3.1 | D-aspartate |
| D-glutamate oxidase | EC 1.4.3.7 | D-glutamate |
| D-glutamate(D-aspartate) oxidase | EC 1.4.3.15 | D-glutamate |
| dihydrobenzophenanthridine oxidase | EC 1.5.3.12 | dihydrosanguinarine |
| dihydroorotate oxidase | EC 1.3.3.1 | (S)-dihydroorotate |
| dihydrouracil oxidase | EC 1.3.3.7 | 5,6-dihydrouracil |
| dimethylglycine oxidase | EC 1.5.3.10 | N,N-dimethylglycine |
| D-mannitol oxidase | EC 1.1.3.40 | Mannitol |
| Ecdysone oxidase | EC 1.1.3.16 | Ecdysone |
| ethanolamine oxidase | EC 1.4.3.8 | Ethanolamine |
| Galactose oxidase | EC 1.1.3.9 | D-galactose |
| Glucose oxidase | EC 1.1.3.4 | β-D-glucose |
| glutathione oxidase | EC 1.8.3.3 | Glutathione |
| Glycerol-3-phosphate oxidase | EC 1.1.3.21 | sn-glycerol 3-phosphate |
| Glycine oxidase | EC 1.4.3.19 | Glycine |
| glyoxylate oxidase | EC 1.2.3.5 | Glyoxylate |
| hexose oxidase | EC 1.1.3.5 | D-glucose, D-galactose |

TABLE 1-continued

| ACCEPTED COMMON NAME | IUBMB ENZYME NOMEN-CLATURE | PREFERRED SUBSTRATE |
|---|---|---|
| | | D-mannose |
| | | maltose |
| | | lactose |
| | | cellobiose |
| hydroxyphytanate oxidase | EC 1.1.3.27 | L-2-hydroxyphytanate |
| indole-3-acetaldehyde oxidase | EC 1.2.3.7 | (indol-3-yl)acetaldehyde |
| lactic acid oxidase | | Lactic acid |
| L-amino-acid oxidase | EC 1.4.3.2 | an L-amino acid |
| L-aspartate oxidase | EC 1.4.3.16 | L-aspartate |
| L-galactonolactone oxidase | EC 1.3.3.12 | L-galactono-1,4-lactone |
| L-glutamate oxidase | EC 1.4.3.11 | L-glutamate |
| L-gulonolactone oxidase | EC 1.1.3.8 | L-gulono-1,4-lactone |
| L-lysine 6-oxidase | EC 1.4.3.20 | L-lysine |
| L-lysine oxidase | EC 1.4.3.14 | L-lysine |
| long-chain-alcohol oxidase | EC 1.1.3.20 | A long-chain-alcohol |
| L-pipecolate oxidase | EC 1.5.3.7 | L-pipecolate |
| L-sorbose oxidase | EC 1.1.3.11 | L-sorbose |
| malate oxidase | EC 1.1.3.3 | (S)-malate |
| methanethiol oxidase | EC 1.8.3.4 | Methanethiol |
| monoamino acid oxidase | | |
| $N^6$-methyl-lysine oxidase | EC 1.5.3.4 | 6-N-methyl-L-lysine |
| N-acylhexosamine oxidase | EC 1.1.3.29 | N-acetyl-D-glucosamine |
| | | N-glycolylglucosamine |
| | | N-acetylgalactosamine |
| | | N-acetylmannosamine. |
| NAD(P)H oxidase | EC 1.6.3.1 | NAD(P)H |
| nitroalkane oxidase | EC 1.7.3.1 | a nitroalkane |
| N-methyl-L-amino-acid oxidase | EC 1.5.3.2 | an N-methyl-L-amino acid |
| nucleoside oxidase | EC 1.1.3.39 | Adenosine |
| Oxalate oxidase | EC 1.2.3.4 | Oxalate |
| polyamine oxidase | EC 1.5.3.11 | 1-N-acetylspermine |
| polyphenol oxidase | EC 1.14.18.1 | |
| Polyvinyl-alcohol oxidase | EC 1.1.3.30 | polyvinyl alcohol |
| prenylcysteine oxidase | EC 1.8.3.5 | an S-prenyl-L-cysteine |
| Protein-lysine 6-oxidase | EC 1.4.3.13 | peptidyl-L-lysyl-peptide |
| putrescine oxidase | EC 1.4.3.10 | butane-1,4-diamine |
| Pyranose oxidase | EC 1.1.3.10 | D-glucose |
| | | D-xylose |
| | | L-sorbose |
| | | D-glucono-1,5-lactone |
| Pyridoxal 5'-phosphate synthase | EC 1.4.3.5 | pyridoxamine 5'-phosphate |
| pyridoxine 4-oxidase | EC 1.1.3.12 | Pyridoxine |
| pyrroloquinoline-quinone synthase | EC 1.3.3.11 | 6-(2-amino-2-carboxyethyl)-7,8-dioxo-1,2,3,4,5,6,7,8-octahydroquinoline-2,4-dicarboxylate |
| Pyruvate oxidase | EC 1.2.3.3 | Pyruvate |
| Pyruvate oxidase (CoA-acetylating) | EC 1.2.3.6 | Pyruvate |
| Reticuline oxidase | EC 1.21.3.3 | Reticuline |
| retinal oxidase | EC 1.2.3.11 | Retinal |
| Rifamycin-B oxidase | EC 1.10.3.6 | rifamycin-B |
| Sarcosine oxidase | EC 1.5.3.1 | Sarcosine |
| secondary-alcohol oxidase | EC 1.1.3.18 | a secondary alcohol |
| sulfite oxidase | EC 1.8.3.1 | Sulfite |
| superoxide dismutase | EC 1.15.1.1 | Superoxide |
| superoxide reductase | EC 1.15.1.2 | Superoxide |
| tetrahydroberberine oxidase | EC 1.3.3.8 | (S)-tetrahydroberberine |
| Thiamine oxidase | EC 1.1.3.23 | Thiamine |
| tryptophan α,β-oxidase | EC 1.3.3.10 | L-tryptophan |
| urate oxidase (uricase, uric acid oxidase) | EC 1.7.3.3 | uric acid |
| Vanillyl-alcohol oxidase | EC 1.1.3.38 | vanillyl alcohol |
| Xanthine oxidase | EC 1.17.3.2 | Xanthine |
| xylitol oxidase | EC 1.1.3.41 | Xylitol | e) Autoantibody

As used herein, the phrase "autoantibody" refers to an antibody that binds to an analyte that is endogenously produced in the subject in which the antibody is produced.

f) Antibody-Analyte Complex

As used herein, the phrase "antibody-analyte complex" refers to a combination of an antibody and an antigen, in which the antigen is an analyte of interest, and the antibody and antigen are bound by specific, noncovalent interactions between an antigen-combining site on the antibody and an antigen epitope. The antigen may be a protein or other molecule. The term "autoantibody-analyte complex" encompasses an antibody-analyte complex in which the antibody is an antibody that binds to an analyte that is endogenously produced in the subject in which the antibody is produced.

g) Detectable Label

As used herein the term "detectable label" refers to any moiety that generates a measurable signal via optical, electrical, or other physical indication of a change of state of a molecule or molecules coupled to the moiety. Such physical indicators encompass spectroscopic, photochemical, biochemical, immunochemical, electromagnetic, radiochemical, and chemical means, such as but not limited to fluorescence, chemifluorescence, chemiluminescence, and the like. Preferred detectable labels include acridinium compounds such as an acridinium-9-carboximide having a structure according to Formula I as set forth in section B herein below, and an acridinium-9-carboxylate aryl ester having a structure according to Formula II as also set forth in section B herein below.

h) Subject

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc.) and a human). Preferably, the subject is a human.

i) Test Sample

As used herein, the term "test sample" generally refers to a biological material being tested for and/or suspected of containing an analyte of interest and which may also include autoantibodies to the analyte of interest. The biological material may be derived from any biological source but preferably is a biological fluid likely to contain the analyte of interest. Examples of biological materials include, but are not limited to, stool, whole blood, serum, plasma, red blood cells, platelets, interstitial fluid, saliva, ocular lens fluid, cerebral spinal fluid, sweat, urine, ascites fluid, mucous, nasal fluid, sputum, synovial fluid, peritoneal fluid, vaginal fluid, menses, amniotic fluid, semen, soil, etc. The test sample may be used directly as obtained from the biological source or following a pretreatment to modify the character of the sample. For example, such pretreatment may include preparing plasma from blood, diluting viscous fluids and so forth. Methods of pretreatment may also involve filtration, precipitation, dilution, distillation, mixing, concentration, inactivation of interfering components, the addition of reagents, lysing, etc. If such methods of pretreatment are employed with respect to the test sample, such pretreatment methods are such that the analyte of interest remains in the test sample at a concentration proportional to that in an untreated test sample (e.g., namely, a test sample that is not subjected to any such pretreatment method(s)).

B. IMMUNOASSAY FOR DETECTING AN ANALYTE OF INTEREST IN A TEST SAMPLE THAT MAY CONTAIN AUTOANTIBODIES

The present disclosure relates to an immunoassay for detecting an analyte of interest in a test sample in which autoantibodies against the analyte of interest may or may not be present. Examples of analytes of interest for which autoantibodies have been described include but are not limited to cardiac troponin, myeloperoxidase (MPO), prostate specific antigen (PSA), and thyroid stimulating hormone (TSH). It will be understood that the immunoassays described herein are also applicable to the detection of any other analyte of interest for which autoantibodies not yet described create the risk of interference for immunodetection of the analyte.

The immunoassay of the present disclosure involves obtaining a test sample from a subject and then detecting the presence of an analyte of interest using immunodetection while compensating for the presence of any autoantibodies against the analyte that may be present in the sample. This is achieved in part by providing a solid phase, which can be a solid support, on which a first, capture antibody is immobilized, and which also during the course of the immunoassay binds any autoantibody that may be present in the sample.

Immunoassay Methods

The immunoassay methods of the present disclosure can be carried out in any of a wide variety of formats. A general review of immunoassays is available in METHODS IN CELL BIOLOGY VOLUME 37: ANTIBODIES IN CELL BIOLOGY, Asai, ed. Academic Press, Inc. New York (1993), and BASIC AND CLINICAL IMMUNOLOGY 7TH EDITION, Stites & Terr, eds. (1991), which are herein incorporated by reference in its entirety. FIG. 1 is a schematic diagram of a typical heterogeneous sandwich immunoassay employing a solid phase (as a solid support) to which is bound a first (capture) antibody reactive with at least one epitope on the analyte of interest. A second (detection) antibody is also reactive with at least one epitope on the analyte of interest. As is shown in FIG. 1, the second antibody may be conjugated to a detectable label (as indicated by the starburst icon) that provides a signal that is measured after the detection antibody binds to the captured analyte. When a test sample containing the analyte of interest contacts the first antibody, the first antibody captures the analyte. The analyte is contacted with the second antibody resulting in the formation of an immunodetection complex consisting of the first antibody, analyte and second antibody, and the complex is bound to the solid phase. The signal generated by the second (detection) antibody is proportional to the concentration of the analyte as determined by the rate of formation ($k_1$) of the immunodetection complex versus the rate of dissociation of the immunodetection complex ($k_2$). As can be inferred from FIG. 1, autoantibodies, which if present are unpredictable as to exactly where on an analyte they will bind, can substantially interfere with binding of the first and/or second antibody, and thus with the resulting signal.

Figure 2:
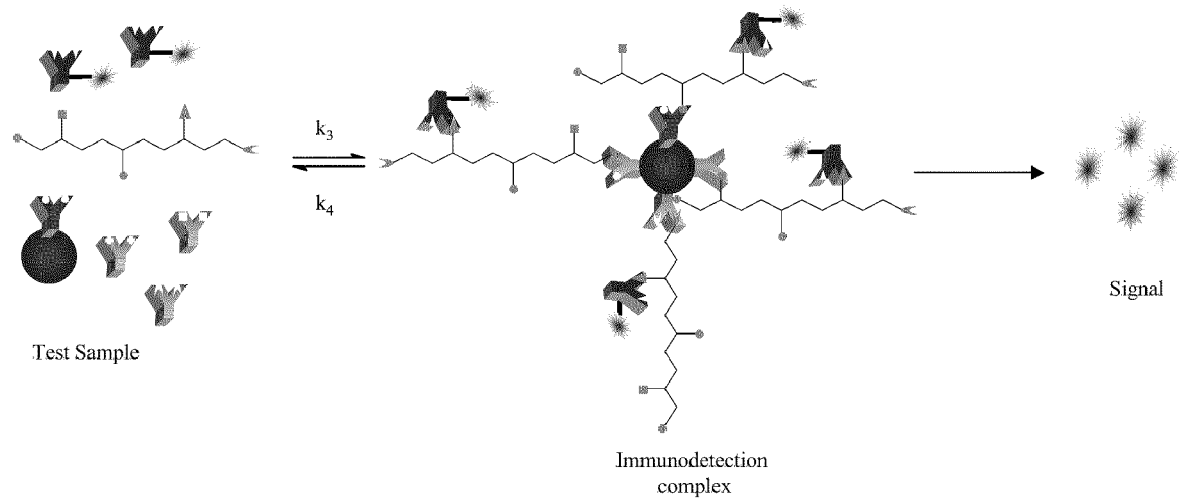
FIG. 2 shows a schematic diagram of an immunoassay reaction sequence in which autoantibodies reactive with a target analyte and autoantibodies unrelated to the target analyte are bound to a solid phase bearing an exogenous capture antibody.

In contrast to an immunoassay format as described and illustrated in FIG. 1, immunoassays according to the present disclosure employ a solid phase that bears a first (capture) antibody as in FIG. 1, but also is capable of binding any autoantibodies that may be present in the test sample. FIG. 2 is a schematic diagram of an immunoassay format according to the present disclosure, in which the test sample contains multiple autoantibodies as shown, each reactive with at least one different epitope on the analyte of interest. The test sample may also contain autoantibodies that are unrelated to the analyte (not shown). As shown in FIG. 2, the solid phase captures the analyte via binding of the analyte to the first antibody, but also by directly binding autoantibodies that are reactive with the analyte (as well as any unrelated autoantibodies that are not reactive with the analyte). The result under appropriate conditions is formation of an immunodetection complex that includes a first antibody-analyte-second antibody complex, and an autoantibody-analyte-second antibody complex, which generates a stronger signal than that produced by the immunodetection complex shown in FIG. 1. In the immunoassay of the present disclosure and as shown in FIG. 2, the signal generated by the second (detection) antibody remains proportional to the concentration of the analyte as determined by the rate of formation ($k_3$) of the new immunodetection complex versus the rate of dissociation of the new immunodetection complex ($k_4$). In test samples containing no autoantibodies reactive with the analyte, autoantibodies unrelated to the analyte are bound by the solid support, but hey do not bind any of the analyte of interest and the signal indicative of the analyte is unaffected.

Thus, according to the present disclosure, an immunoassay of the present disclosure to detect the presence of an analyte of interest is a heterogeneous assay employing a solid phase which can be a solid support. The immunoassay can be performed for example by immobilizing a first antibody on the solid phase, wherein the first antibody is an exogenous capture antibody, i.e. an exogenous antibody that is reactive with at least one epitope on the analyte of interest. The solid phase is also capable of binding any endogenous autoantibodies that may be present in the sample. Under conditions sufficient for specific binding of the first antibody to the analyte of interest, the test sample suspected of containing the analyte of interest, and which may or may not contain autoantibodies, is contacted with the first (capture) antibody, thus forming a first antibody-analyte complex. In the case of a test sample containing at least one autoantibody against the analyte, the autoantibody binds to the solid phase and also can bind to at least one epitope on the analyte to form an autoantibody-analyte complex. A mixture thus formed of the first antibody-analyte complex and the autoantibody-analyte complex is contacted with a second, detection antibody that binds to at least one epitope on the analyte of interest. This step is carried out under conditions sufficient for specific binding of the second antibody to any of the analyte of interest that is present in the test sample. The second antibody binds to the analyte to form an immunodetection complex which forms a measurable assembly including the first antibody-analyte-second antibody complex and the autoantibody-analyte-second antibody complex. By "measurable assembly" is meant a configuration of molecules that when formed generates a signal susceptible to physical detection and/or quantification. In certain embodiments for example, the second antibody may be labeled with a detectable label. Depending on the detection approach used, an optical, electrical, or change-of-state signal of the assembly is measured.

Although the immunoassay is described above as including a sequence of steps for illustrative purposes, the test sample may be contacted with the first (capture) antibody and the second (detection) antibody simultaneously or sequentially, in any order. Regardless of the order of contact, if autoantibodies are present in the sample, the autoantibodies bind directly to the solid phase. Only those autoantibodies that are reactive with the analyte of interest form part of the immunodetection complex that contains the analyte bound to the first, capture antibody, any autoantibody reactive with the analyte, and the second, detection antibody.

In one format of a sandwich immunoassay according to the present disclosure, detecting comprises detecting a signal from the solid phase-affixed immunodetection complex which is a measurable assembly including a first antibody-analyte-second antibody complex and an autoantibody-analyte-second antibody complex. In one embodiment, the immunodetection complex is separated from the solid phase, typically by washing, and the signal from the bound label is detected. In another format of a sandwich immunoassay according to the present disclosure, the immunodetection complex remains a solid phase-affixed complex, which is then detected.

Antibodies

In the immunoassays according to the present disclosure, the first antibody can be a polyclonal antibody, a monoclonal antibody, a chimeric antibody, a human antibody, an affinity maturated antibody or an antibody fragment. Similarly, the second antibody can be a polyclonal antibody, a monoclonal antibody, a chimeric antibody, a human antibody, an affinity maturated antibody or an antibody fragment.

While monoclonal antibodies are highly specific to the analyte/antigen, a polyclonal antibody can preferably be used as the capture (first) antibody to immobilize as much of the analyte/antigen as possible. A monoclonal antibody with inherently higher binding specificity for the analyte/antigen may then preferably be used as the detection (second) antibody. In any case, the capture and detection antibodies preferably recognize two non-overlapping epitopes on the analyte to avoid blockage of, or interference by the capture antibody with the epitope recognized by the detection antibody. Preferably the capture and detection antibodies are capable of binding simultaneously to different epitopes on the analyte, each without interfering with the binding of the other.

Polyclonal antibodies are raised by injecting (e.g., subcutaneous or intramuscular injection) an immunogen into a suitable non-human mammal (e.g., a mouse or a rabbit). Generally, the immunogen should induce production of high titers of antibody with relatively high affinity for the target antigen.

If desired, the antigen may be conjugated to a carrier protein by conjugation techniques that are well known in the art. Commonly used carriers include keyhole limpet hemocyanin (KLH), thyroglobulin, bovine serum albumin (BSA), and tetanus toxoid. The conjugate is then used to immunize the animal.

The antibodies are then obtained from blood samples taken from the animal. The techniques used to produce polyclonal antibodies are extensively described in the literature (see, e.g., Methods of Enzymology, "Production of Antisera With Small Doses of Immunogen: Multiple Intradermal Injections," Langone, et al. eds. (Acad. Press, 1981)). Polyclonal antibodies produced by the animals can be further purified, for example, by binding to and elution from a matrix to which the target antigen is bound. Those of skill in the art will know of various techniques common in the immunology arts for purification and/or concentration of polyclonal, as well as monoclonal, antibodies (see, e.g., Coligan, et al. (1991) Unit 9, Current Protocols in Immunology, Wiley Interscience).

For many applications, monoclonal antibodies (mAbs) are preferred. The general method used for production of hybridomas secreting mAbs is well known (Kohler and Milstein (1975) Nature, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody that bound to cancer cell lines. Confirmation of specificity among mAbs can be accomplished using routine screening techniques (such as the enzyme-linked immunosorbent assay, or "ELISA") to determine the elementary reaction pattern of the mAb of interest.

As used herein, the term "antibody" encompasses antigen-binding antibody fragments, e.g., single chain antibodies (scFv or others), which can be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348: 552-554; Hoogenboom et al. (1991) Nucleic Acids Res. 19: 4133-4137).

Since the antibody fragments on the surface of the phage are functional, phage-bearing antigen-binding antibody fragments can be separated from non-binding phage by antigen affinity chromatography (McCafferty et al. (1990) Nature, 348: 552-554). Depending on the affinity of the antibody fragment, enrichment factors of 20-fold-1,000,000-fold are obtained for a single round of affinity selection. By infecting bacteria with the eluted phage, however, more phage can be grown and subjected to another round of selection. In this way, an enrichment of 1000-fold in one round can become 1,000,000-fold in two rounds of selection (McCafferty et al. (1990) Nature, 348: 552-554). Thus, even when enrichments are low (Marks et al. (1991) J. Mol. Biol. 222: 581-597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) J. Mol. Biol. 222: 581-597). In one embodiment, natural VH and VL repertoires present in human peripheral blood lymphocytes are isolated from unimmunized donors by PCR. The V-gene repertoires can be spliced together at random using PCR to create a scFv gene repertoire which can be cloned into a phage vector to create a library of 30 million phage antibodies (Id.). From a single "naive" phage antibody library, binding antibody fragments have been isolated against more than 17 different antigens, including haptens, polysaccharides, and proteins (Marks et al. (1991) J. Mol. Biol. 222: 581-597; Marks et al. (1993). Bio/Technology. 10: 779-783; Griffiths et al. (1993) EMBO J. 12: 725-734; Clackson et al. (1991) Nature. 352: 624-628). Antibodies have been produced against self proteins, including human thyroglobulin, immunoglobulin, tumor necrosis factor, and CEA (Griffiths et al. (1993) EMBO J. 12: 725-734). The antibody fragments are highly specific for the antigen used for selection and have affinities in the 1 nM to 100 nM range (Marks et al. (1991) J. Mol. Biol. 222: 581-597; Griffiths et al. (1993) EMBO J. 12: 725-734). Larger phage antibody libraries result in the isolation of more antibodies of higher binding affinity to a greater proportion of antigens.

As those of skill in the art readily appreciate, antibodies can be prepared by any of a number of commercial services (e.g., Berkeley Antibody Laboratories, Bethyl Laboratories, Anawa, Eurogenetec, etc.).

Solid Phase

The solid phase can be any suitable material with sufficient surface affinity to bind a capture antibody and autoantibodies present in the test sample. The solid phase can take any of a number of forms, such as a magnetic particle, bead, test tube, microtiter plate, cuvette, membrane, a scaffolding molecule, quartz crystal, film, filter paper, disc or a chip. Useful solid phase materials include: natural polymeric carbohydrates and their synthetically modified, crosslinked, or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen, such as proteins and derivatives, including cross-linked or modified gelatins; natural hydrocarbon polymers, such as latex and rubber; synthetic polymers, such as vinyl polymers, including polyethylene, polypropylene, polystyrene, polyvinylchloride, polyvinylacetate and its partially hydrolyzed derivatives, polyacrylamides, polymethacrylates, copolymers and terpolymers of the above polycondensates, such as polyesters, polyamides, and other polymers, such as polyurethanes or polyepoxides; inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, tubes, particulates, or plates, or they may be coated onto, bonded, or laminated to appropriate inert carriers, such as paper, glass, plastic films, fabrics, or the like. Nitrocellulose has excellent absorption and adsorption qualities for a wide variety of reagents including monoclonal antibodies. Nylon also possesses similar characteristics and also is suitable.

Alternatively, the solid phase can constitute microparticles. Microparticles useful in the present disclosure can be selected by one skilled in the art from any suitable type of particulate material and include those composed of polystyrene, polymethylacrylate, polypropylene, latex, polytetrafluoroethylene, polyacrylonitrile, polycarbonate, or similar materials. Further, the microparticles can be magnetic or paramagnetic microparticles, so as to facilitate manipulation of the microparticle within a magnetic field. In an exemplary embodiment the microparticles are carboxylated magnetic microparticles.

Microparticles can be suspended in the mixture of soluble reagents and test sample or can be retained and immobilized by a support material. In the latter case, the microparticles on or in the support material are not capable of substantial movement to positions elsewhere within the support material. Alternatively, the microparticles can be separated from suspension in the mixture of soluble reagents and test sample by sedimentation or centrifugation. When the microparticles are magnetic or paramagnetic the microparticles can be separated from suspension in the mixture of soluble reagents and test sample by a magnetic field.

The methods of the present disclosure can be adapted for use in systems that utilize microparticle technology including automated and semi-automated systems wherein the solid phase comprises a microparticle. Such systems include those described in pending U.S. application Ser. No. 425,651 and U.S. Pat. No. 5,089,424, which correspond to published EPO App. Nos. EP 0 425 633 and EP 0 424 634, respectively, and U.S. Pat. No. 5,006,309.

In particular embodiments, the solid phase includes one or more electrodes. Capture antibodies can be affixed, directly or indirectly, to the electrode(s). In one embodiment, for example, capture antibodies can be affixed to magnetic or paramagnetic microparticles, which are then positioned in the vicinity of the electrode surface using a magnet. Systems in which one or more electrodes serve as the solid phase are useful where detection is based on electrochemical interactions. Exemplary systems of this type are described, for example, in U.S. Pat. No. 6,887,714 (issued May 3, 2005). The basic method is described further below with respect to electrochemical detection.

The capture antibody can be attached to the solid phase by adsorption, where it is retained by hydrophobic forces. Alternatively, the surface of the solid phase can be activated by chemical processes that cause covalent linkage of the capture antibody to the support.

To change or enhance the intrinsic charge of the solid phase, a charged substance can be coated directly onto the solid phase. Ion capture procedures for immobilizing an immobilizable reaction complex with a negatively charged polymer, described in U.S. application Ser. No. 150,278, corresponding to EP Publication No. 0326100, and U.S. application Ser. No. 375,029 (EP Publication No. 0406473), can be employed according to the present disclosure to affect a fast solution-phase immunochemical reaction. In these procedures, an immobilizable immune complex is separated from the rest of the reaction mixture by ionic interactions between the negatively charged polyanion/immune complex and the previously treated, positively charged matrix and detected by using any of a number of signal-generating systems, including, e.g., chemiluminescent systems, as described in U.S. application Ser. No. 921,979, corresponding to EPO Publication No. 0 273,115.

If the solid phase is silicon or glass, the surface must generally be activated prior to attaching the capture antibody. Activated silane compounds such as triethoxy amino propyl silane (available from Sigma Chemical Co., St. Louis, Mo.), triethoxy vinyl silane (Aldrich Chemical Co., Milwaukee, Wis.), and (3-mercapto-propyl)-trimethoxy silane (Sigma Chemical Co., St. Louis, Mo.) can be used to introduce reactive groups such as amino-, vinyl, and thiol, respectively. Such activated surfaces can be used to link the capture directly (in the cases of amino or thiol), or the activated surface can be further reacted with linkers such as glutaraldehyde, bis (succinimidyl) suberate, SPPD 9 succinimidyl 3-[2-pyridyldithio]propionate), SMCC (succinimidyl-4-[Nmaleimidomethyl]cyclohexane-1-carboxylate), SIAB (succinimidyl[4iodoacetyl]aminobenzoate), and SMPB (succinimidyl 4-[1 maleimidophenyl]butyrate) to separate the capture antibody from the surface. Vinyl groups can be oxidized to provide a means for covalent attachment. Vinyl groups can also be used as an anchor for the polymerization of various polymers such as poly-acrylic acid, which can provide multiple attachment points for specific capture antibodies. Amino groups can be reacted with oxidized dextrans of various molecular weights to provide hydrophilic linkers of different size and capacity. Examples of oxidizable dextrans include Dextran T-40 (molecular weight 40,000 daltons), Dextran T-110 (molecular weight 110,000 daltons), Dextran T-500 (molecular weight 500,000 daltons), Dextran T-2M (molecular weight 2,000,000 daltons) (all of which are available from Pharmacia, Piscataway, N.J.), or Ficoll (molecular weight 70,000 daltons; available from Sigma Chemical Co., St. Louis, Mo.). Additionally, polyelectrolyte interactions can be used to immobilize a specific capture antibody on a solid phase using techniques and chemistries described U.S. application Ser. No. 150,278, filed Jan. 29, 1988, and U.S. application Ser. No. 375,029, filed Jul. 7, 1989, each of which is incorporated herein by reference.

Other considerations affecting the choice of solid phase include the ability to minimize non-specific binding of labeled entities and compatibility with the labeling system employed. For, example, solid phases used with fluorescent labels should have sufficiently low background fluorescence to allow signal detection.

Following attachment of a specific capture antibody, the surface of the solid support may be further treated with materials such as serum, proteins, or other blocking agents to minimize non-specific binding and/or to promote binding of autoantibodies.

Detection Systems In General

As discussed above, immunoassays according to the present disclosure employ a second, detection antibody that is analyte-specific. In certain embodiments, the second antibody has a detectable label.

Detectable labels suitable for use in the detection antibodies of the present disclosure include any compound or composition having a moiety that is detectable by spectroscopic, photochemical, biochemical, immunochemical, electrical, optical, or chemical means. Such labels include, for example, an enzyme, oligonucleotide, nanoparticle chemiluminophore, fluorophore, fluorescence quencher, chemiluminescence quencher, or biotin. Thus for example, in an immunoassay employing an optical signal, the optical signal is measured as an analyte concentration dependent change in chemiluminescence, fluorescence, phosphorescence, electrochemiluminescence, ultraviolet absorption, visible absorption, infrared absorption, refraction, surface plasmon resonance. In an immunoassay employing an electrical signal, the electrical signal is measured as an analyte concentration dependent change in current, resistance, potential, mass to charge ratio, or ion count. In an immunoassay employing a change-of-state signal, the change of state signal is measured as an analyte concentration dependent change in size, solubility, mass, or resonance.

Useful labels according to the present disclosure include magnetic beads (e.g., Dynabeads™), fluorescent dyes (e.g., fluorescein, Texas Red, rhodamine, green fluorescent protein) and the like (see, e.g., Molecular Probes, Eugene, Oreg., USA), chemiluminescent compounds such as acridinium (e.g., acridinium-9-carboxamide), phenanthridinium, dioxetanes, luminol and the like, radiolabels (e.g., $^3H$, $^{125}I$, $^{35}S$, $^{14}C$, or $^{32}P$), catalysts such as enzymes (e.g., horse radish peroxidase, alkaline phosphatase, beta-galactosidase and others commonly used in an ELISA), and colorimetric labels such as colloidal gold (e.g., gold particles in the 40-80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label can be attached to the detection antibody prior to, or during, or after contact with the biological sample. So-called "direct labels" are detectable labels that are directly attached to or incorporated into the detection antibody prior to use in the assay. Direct labels can be attached to or incorporated into the detection antibody by any of a number of means well known to those of skill in the art.

In contrast, so-called "indirect labels" typically bind to the detection antibody at some point during the assay. Often, the indirect label binds to a moiety that is attached to or incorporated into the detection agent prior to use. Thus, for example, a detection antibody can be biotinylated before use in an assay. During the assay, an avidin-conjugated fluorophore can bind the biotin-bearing detection agent, to provide a label that is easily detected.

In another example of indirect labeling, polypeptides capable of specifically binding immunoglobulin constant regions, such as polypeptide A or polypeptide G, can also be used as labels for detection antibodies. These polypeptides are normal constituents of the cell walls of streptococcal bacteria. They exhibit a strong non-immunogenic reactivity with immunoglobulin constant regions from a variety of species (see, generally Kronval, et al. (1973) J. Immunol., 111: 1401-1406, and Akerstrom (1985) J. Immunol., 135: 2589-2542). Such polypeptides can thus be labeled and added to the assay mixture, where they will bind to the capture and detection antibodies, as well as to the autoantibodies, labeling all and providing a composite signal attributable to analyte and autoantibody present in the sample.

Some labels useful in the present disclosure may require the use of an additional reagent(s) to produce a detectable signal. In an ELISA, for example, an enzyme label (e.g., beta-galactosidase) will require the addition of a substrate (e.g., X-gal) to produce a detectable signal. In immunoassays using an acridinium compound as the direct label, a basic solution and a source of hydrogen peroxide are added.

Detection Systems—Exemplary Formats

Chemiluminescence Immunoassay: In an exemplary embodiment, a chemiluminescent compound is used in the above-described methods as a direct label conjugated to the second, detection antibody. The chemiluminescent compound can be an acridinium compound. When an acridinium compound is used as the detectable label, then the above-described method may further include generating or providing a source of hydrogen peroxide to the mixture resulting from contacting the test sample with the first antibody and the second antibody, and adding at least one basic solution to the mixture to generate a light signal. The light signal generated or emitted by the mixture is then measured to detect the analyte of interest in the test sample.

The source of hydrogen peroxide may be a buffer solution or a solution containing hydrogen peroxide or an enzyme that generates hydrogen peroxide when added to the test sample. The basic solution serves as a trigger solution, and the order in which the at least one basic solution and detectable label are added is not critical. The basic solution used in the method is a solution that contains at least one base and that has a pH greater than or equal to 10, preferably, greater than or equal to 12. Examples of basic solutions include, but are not limited to, sodium hydroxide, potassium hydroxide, calcium hydroxide, ammonium hydroxide, magnesium hydroxide, sodium carbonate, sodium bicarbonate, calcium hydroxide, calcium carbonate and calcium bicarbonate. The amount of basic solution added to the test sample depends on the concentration of the basic solution used in the assay. Based on the concentration of the basic solution used, one skilled in the art could easily determine the amount of basic solution to be used in the method described herein.

In a chemiluminescence immunoassay according to the present disclosure and using an acridinium compound as the detectable label, preferably the acridinium compound is an acridinium-9-carboxamide. Specifically, the acridinium-9-carboxamide has a structure according to formula I:

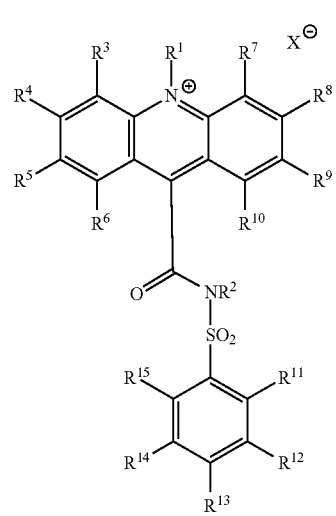

wherein R¹ and R² are each independently selected from the group consisting of: alkyl, alkenyl, alkynyl, aryl or aralkyl, sulfoalkyl, carboxyalkyl and oxoalkyl, and wherein R³ through R¹⁵ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and further wherein any of the alkyl, alkenyl, alkynyl, aryl or aralkyl may contain one or more heteroatoms; and optionally, if present, X<sup>⊖</sup> is an anion.

Methods for preparing acridinium 9-carboxamides are described in Mattingly, P. G. *J. Biolumin. Chemilumin.*, 6, 107-14; (1991); Adamczyk, M.; Chen, Y.-Y., Mattingly, P. G.; Pan, Y. *J. Org. Chem.*, 63, 5636-5639 (1998); Adamczyk, M.; Chen, Y.-Y.; Mattingly, P. G.; Moore, J. A.; Shreder, K. *Tetrahedron*, 55, 10899-10914 (1999); Adamczyk, M.; Mattingly, P. G.; Moore, J. A.; Pan, Y. *Org. Lett.*, 1, 779-781 (1999); Adamczyk, M.; Chen, Y.-Y.; Fishpaugh, J. R.; Mattingly, P. G.; Pan, Y.; Shreder, K.; Yu, Z. *Bioconjugate Chem.*, 11, 714-724 (2000); Mattingly, P. G.; Adamczyk, M. In *Luminescence Biotechnology: Instruments and Applications*; Dyke, K. V. Ed.; CRC Press: Boca Raton, pp. 77-105 (2002); Adamczyk, M.; Mattingly, P. G.; Moore, J. A.; Pan, Y. *Org. Lett.*, 5, 3779-3782 (2003); and U.S. Pat. Nos. 5,468,646, 5,543,524 and 5,783,699 (each incorporated herein by reference in their entireties for their teachings regarding same).

Alternatively, the acridinium compound can be an acridinium-9-carboxylate aryl ester; the acridinium-9-carboxylate aryl ester can have a structure according to formula II:

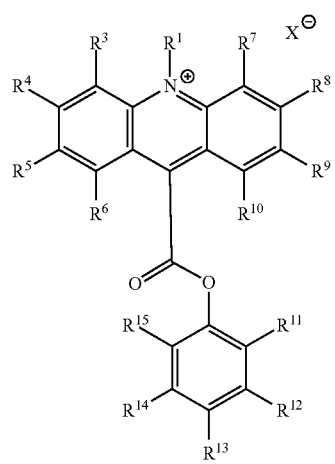

II wherein R¹ is an alkyl, alkenyl, alkynyl, aryl or aralkyl, sulfoalkyl, carboxyalkyl and oxoalkyl; and wherein R³ through R¹⁵ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, X<sup>⊖</sup> is an anion.

Examples of acridinium-9-carboxylate aryl esters having the above formula II that can be used in the present disclosure include, but are not limited to, 10-methyl-9-(phenoxycarbonyl)acridinium fluorosulfonate (available from Cayman Chemical, Ann Arbor, Mich.). Methods for preparing acridinium 9-carboxylate aryl esters are described in McCapra, F., et al., *Photochem. Photobiol.*, 4, 1111-21 (1965); Razavi, Z et al., *Luminescence*, 15:245-249 (2000); Razavi, Z et al., *Luminescence*, 15:239-244 (2000); and U.S. Pat. No. 5,241, 070 (each incorporated herein by reference in their entireties for their teachings regarding same).

In addition to the at least one acridinium compound, the indicator solution can also contain at least one surfactant. Any surfactant that when dissolved in water, lowers the surface tension of the water and increases the solubility of organic compounds, can be used in the present invention. Examples of surfactants that can be used is one or more non-ionic or ionic surfactants (e.g., anionic, cationic or zwitterionic surfactants). Examples of non-ionic surfactants that can be used include, but are not limited to, t-octylpheoxypolyethoxyethanol (TRITON X-100, Sigma Aldrich, St. Louis, Mo.), polyoxyethylenesorbitan monolaurate (Tween 20), nonylphenol polyoxyethylene ether (Nonidet P10), decyldimethylphosphine oxide (APO-10), Cyclohexyl-n-ethyl-β-D-Maltoside, Cyclohexyl-n-hexyl-β-D-Maltoside, Cyclohexyl-n-methyl-β-D-Maltoside, n-Decanoylsucrose, n-Decyl-β-D-glucopyranoside, n-Decyl-β-D-maltopyranoside, n-Decyl-β-D-thiomaltoside, Digitonin, n-Dodecanoyl sucrose, n-Dodecyl-β-D-glucopyranoside, n-Dodecyl-β-D-maltoside, polyoxyethylene (10) dodecyl ether (Genapol C-100), isotridecanol polyglycol ether (Genapol X-80), isotridecanol polyglycol ether (Genapol X-100), Heptane-1,2,3-triol, n-Heptyl-β-D-glucopyranoside, n-Heptyl-β-D-thioglucopyranoside and combinations thereof. An example of a ionic surfactant that can be used include, sodium cholate, chenodeoxycholic acid, cholic acid, dehydrocholic acid, docusate sodium, docusate sodium salt, glycocholic acid hydrate, glycodeoxycholic acid monohydrate, glycolithocholic acid ethyl ester, N-lauroylsarcosine sodium salt, N-lauroylsarcosine, lithium dodecyl sulfate, calcium propionate, 1-octanesulfonic acid sodium salt, sodium 1-butanesulfonate, sodium chenodeoxycholate, sodium cholate hydrate, sodium 1-decanesulfonate, sodium 1-decanesulfonate, sodium deoxycholate, sodium deoxycholate monohydrate, sodium dodecylbenzenesulfonate, sodium dodecyl sulfate, sodium glycochenodeoxycholate, sodium glycocholate hydrate, sodium 1-heptanesulfonate, sodium hexanesulfonate, sodium 1-nonanesulfonate, sodium octyle sulfate, sodium pentanesulfonate, sodium 1-propanesulfonate hydrate, sodium taurodeoxycholate hydrate, sodium taurohyodeoxycholate hydrate, sodium tauroursodeoxycholate, taurocholic acid sodium salt hydrate, taurolithocholic acid 3-sulfate disodium salt, Triton® X-200, Triton® QS-15, Triton® QS-44, Triton® XQS-20, Trizma® dodecyl sulfate, ursodeoxycholic acid, alkyltrimethylammonium bromide, amprolium hydrocholoride, benzalkonium chloride, benzethonium hydroxide, benzyldimethylhexadecylammonium chloride, benzyldodecyldimethylammonium bromide, choline p-toluenesulfonate salt, dimethyldioctadecylammonium bromide, dodecylethyldimethylammonium bromide, dodecyltrimethylammonium bromide, ethylhexadecyldimethylammonium bromide, Ggirard's reagent, hexadecylpyridinium bromide, hexadecylpyridinium chloride monohydrate, hexadecylpyridinium chloride monohydrate, hexadecyltrimethylammonium bromide, hexadecyltrimethylammonium p-toluenesulfonate, hexadecyltrimethylammonium bromide, hexadecyltrimethylammonium p-toluenesulfonate, Hyamine® 1622, methylbenzethonium chloride, myristyltrimethylammonium bromide, oxyphenonium bromide, N,N',N'-polyoxyethylene (10)-N-tallow-1,3-diaminopropane, tetraheptylammonium bromide, tetrakis(decyl)ammonium bromide, thonzonium bromide and Luviquat™ FC370, Luviquat™ HM 552, Luviquat™ HOLD, Luviquat™ MS 370, Luviquat™ PQ 11PN and combinations thereof (all available from Sigma Aldrich, St. Louis, Mo.).

Optionally, the test sample may be treated prior to the addition of any one or more of the at least one basic solution, hydrogen peroxide source and detectable label. Such treatment may include dilution, ultrafiltration, extraction, precipitation, dialysis, chromatography and digestion. Such treatment may be in addition to and separate from any pretreatment that the test sample may receive or be subjected to as discussed previously herein. Moreover, if such treatment methods are employed with respect to the test sample, such treatment methods are such that the analyte of interest remains in the test sample at a concentration proportional to that in an untreated test sample (e.g., namely, a test sample that is not subjected to any such treatment method(s)).

As mentioned briefly previously herein, the time and order in which the test sample, the at least one basic solution, source of hydrogen peroxide and the detectable label are added to form a mixture is not critical. Additionally, the mixture formed by the at least one basic solution, hydrogen peroxide source and the detectable label, can optionally be allowed to incubate for a period of time. For example, the mixture can be allowed to incubate for a period of time of from about 1 second to about 60 minutes. Specifically, the mixture can be allowed to incubate for a period of from about 1 second to about 18 minutes.

When a chemiluminescent detectable label is used, after the addition of the at least one basic solution, hydrogen peroxide source, and the detectable label to the test sample, a detectable signal, namely, a chemiluminescent signal, is generated. The signal generated by the mixture is detected for a fixed duration of time. Preferably, the mixture is formed and the signal is detected concurrently. The duration of the detection may range from about 0.01 to about 360 seconds, more preferably from about 0.1 to about 30 seconds, and most preferably from about 0.5 to about 5 seconds. Chemiluminescent signals generated can be detected using routine techniques known to those skilled in the art.

Thus, in a chemiluminescent immunoassay according to the present disclosure, a chemiluminescent detectable label is used and added to the test sample, the chemiluminescent signal generated after the addition of the basic solution and the detectable label indicates the presence of the analyte of interest in the test sample, which signal can be detected. The amount or concentration of the analyte of interest in the test sample can be quantified based on the intensity of the signal generated. Specifically, the amount of the analyte of interest contained in a test sample is proportional to the intensity of the signal generated. Specifically, the amount of the analyte of interest present can be quantified based on comparing the amount of light generated to a standard curve for the analyte of interest or by comparison to a reference standard. The standard curve can be generated using serial dilutions or solutions to the analyte of interest of known concentration, by mass spectroscopy, gravimetrically and by other techniques known in the art.

Fluorescence Polarization Immunoassay (FPIA): In an exemplary embodiment, a fluorescent label is employed in a fluorescence polarization immunoassay (FPIA) according to the invention. Generally, fluorescent polarization techniques are based on the principle that a fluorescent label, when excited by plane-polarized light of a characteristic wavelength, will emit light at another characteristic wavelength (i.e., fluorescence) that retains a degree of the polarization relative to the incident light that is inversely related to the rate of rotation of the label in a given medium. As a consequence of this property, a label with constrained rotation, such as one bound to another solution component with a relatively lower rate of rotation, will retain a relatively greater degree of polarization of emitted light than when free in solution.

This technique can be employed in immunoassays according to the invention, for example, by selecting reagents such that binding of the fluorescently labeled entities forms a complex sufficiently different in size such that a change in the intensity light emitted in a given plane can be detected. For example, when a labeled cardiac troponin antibody is bound by one or more cardiac troponin antigens captured by the capture antibody and/or autoantibodies reactive with the cardiac troponin, the resulting complex is sufficiently larger, and its rotation is sufficiently constrained, relative to the free labeled cardiac troponin antibody that binding is easily detected.

Fluorophores useful in FPIA include fluorescein, aminofluorescein, carboxyfluorescein, and the like, preferably 5 and 6-aminomethylfluorescein, 5 and 6-aminofluorescein, 6-carboxyfluorescein, 5-carboxyfluorescein, thioureafluorescein, and methoxytriazinolyl-aminofluorescein, and similar fluorescent derivatives. Examples of commercially available automated instruments with which fluorescence polarization assays can be conducted include: the IMx system, the TDx system, and TDxFLx system (all available from Abbott Laboratories, Abbott Park, Ill.).

Scanning Probe Microscopy (SPM): The use of scanning probe microscopy (SPM) for immunoassays also is a technology to which the immunoassay methods of the present disclosure are easily adaptable. In SPM, in particular in atomic force microscopy, the capture antibody is affixed to the solid phase that in addition to being capable of binding autoantibodies, has a surface suitable for scanning The capture antibody can, for example, be adsorbed to a plastic or metal surface. Alternatively, the capture antibody can be covalently attached to, e.g., derivatized plastic, metal, silicon, or glass according to methods known to those of ordinary skill in the art. Following attachment of the capture antibody, the test sample is contacted with the solid phase, and a scanning probe microscope is used to detect and quantify solid phase-affixed complexes. The use of SPM eliminates the need for labels that are typically employed in immunoassay systems. Such a system is described in U.S. application Ser. No. 662, 147, which is incorporated herein by reference.

MicroElectroMechanical Systems (MEMS): Immunoassays according to the present disclosure can also be carried out using a MicroElectroMechanical System (MEMS). MEMS are microscopic structures integrated onto silicon that combine mechanical, optical, and fluidic elements with electronics, allowing convenient detection of an analyte of interest. An exemplary MEMS device suitable for use in the present disclosure is the Protiveris' multicantilever array. This array is based on chemo-mechanical actuation of specially designed silicon microcantilevers and subsequent optical detection of the microcantilever deflections. When coated on one side with a binding partner, a microcantilever will bend when it is exposed to a solution containing the complementary molecule. This bending is caused by the change in the surface energy due to the binding event. Optical detection of the degree of bending (deflection) allows measurement of the amount of complementary molecule bound to the microcantilever.

Electrochemical Detection Systems: In other embodiments, immunoassays according to the present disclosure are carried out using electrochemical detection, the techniques for which are well known to those skilled in the art. Such electrochemical detection often employs one or more electrodes connected to a device that measures and records an electrical current. Such techniques can be realized in a number of commercially available devices, such as the I-STAT® (Abbott Laboratories, Abbott Park, Ill.) system, which comprises a hand-held electrochemical detection instrument and self-contained assay-specific reagent cartridges. For example, in the present invention, the basic trigger solution could be contained in the self-contained hemoglobin reagent cartridge and upon addition of the test sample, a current would be generated at at least one electrode that is proportional to the amount of hemoglobin in the test sample. A basic procedure for electrochemical detection has been described for example by Heineman and coworkers. This entailed immobilization of a primary antibody (Ab, rat-anti mouse IgG), followed by exposure to a sequence of solutions containing the antigen (Ag, mouse IgG), the secondary antibody conjugated to an enzyme label (AP-Ab, rat anti mouse IgG and alkaline phosphatase), and p-aminophenyl phosphate (PAPP). The AP converts PAPP to p-aminophenol ($PAP_R$, the "R" is intended to distinguish the reduced form from the oxidized form, $PAP_O$, the quinoneimine), which is electrochemically reversible at potentials that do not interfere with reduction of oxygen and water at pH 9.0, where AP exhibits optimum activity. $PAP_R$ does not cause electrode fouling, unlike phenol whose precursor, phenylphosphate, is often used as the enzyme substrate. Although $PAP_R$ undergoes air and light oxidation, these are easily prevented on small scales and short time frames. Picomole detection limits for $PAP_R$ and femtogram detection limits for IgG achieved in microelectrochemical immunoassays using PAPP volumes ranging from 20 µl to 360 µL have been reported previously. In capillary immunoassays with electrochemical detection, the lowest detection limit reported thus far is 3000 molecules of mouse IgG using a volume of 70 µL and a 30 min or 25 min assay time.

In an exemplary embodiment employing electrochemical detection according to the present disclosure, a capture antibody reactive with the analyte of interest can be immobilized on the surface of an electrode which is the solid phase. The electrode is then contacted with a test sample from, e.g., a human. Any analyte in the sample binds to the capture antibody to form a first solid phase-affixed complex. Autoantibodies also bind to the surface of the electrode thereby becoming immobilized on the surface of the electrode. Analyte in the test sample that is unbound by the capture antibody binds to immobilized autoantibodies that are reactive with the analyte to form a second solid phase-affixed complex. These solid phase-affixed complexes are contacted with a detection antibody that is analyte-specific and has a detectable label. Formation of an immunodetection complex including the first antibody-analyte-second antibody complex plus the autoantibody-analyte-second antibody complex results in generation of a signal by the detectable label, which is then detected.

Various electrochemical detection systems are described in U.S. Pat. No. 7,045,364 (issued May 16, 2006; incorporated herein by reference), U.S. Pat. No. 7,045,310 (issued May 16, 2006; incorporated herein by reference), U.S. Pat. No. 6,887,714 (issued May 3, 2005; incorporated herein by reference), U.S. Pat. No. 6,682,648 (issued Jan. 27, 2004; incorporated herein by reference); U.S. Pat. No. 6,670,115 (issued Dec. 30, 2003; incorporated herein by reference).

In the above immunoassay, any acridinium compound can be used. For example, the acridinium compound can be an acridinium-9-carboxamide having a structure according to formula I:

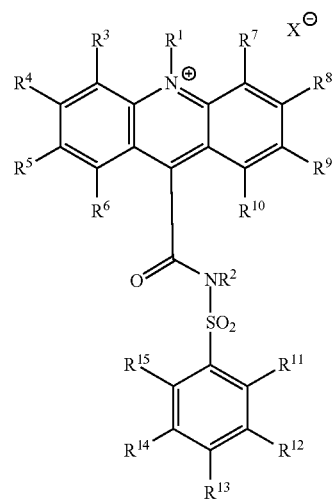

wherein R1 and R2 are each independently selected from the group consisting of: alkyl, alkenyl, alkynyl, aryl or aralkyl, sulfoalkyl, carboxyalkyl and oxoalkyl, and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

Alternatively, the acridinium compound is an acridinium-9-carboxylate aryl ester having a structure according to formula II:

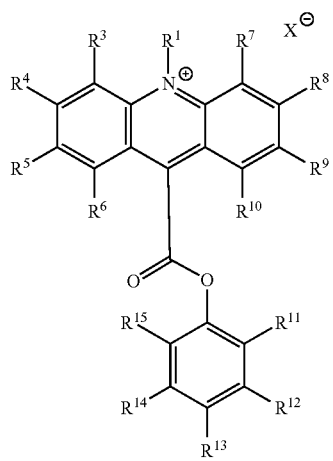

wherein R1 is an alkyl, alkenyl, alkynyl, aryl or aralkyl, sulfoalkyl, carboxyalkyl and oxoalkyl; and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

In the above immunoassay the hydrogen peroxide can be provided by adding a buffer or a solution containing hydrogen peroxide.

In the above immunoassay, the hydrogen peroxide can be generated by adding a hydrogen peroxide generating enzyme to the test sample. The hydrogen peroxide generating enzyme can be selected for example from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, arylaldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

C. KITS

The present disclosure also provides kits for assaying test samples for presence of an analyte of interest wherein the test sample may contain autoantibodies. Kits according to the present disclosure include one or more reagents useful for practicing one or more immunoassays according to the present disclosure. A kit generally includes a package with one or more containers holding the reagents, as one or more separate compositions or, optionally, as admixture where the compatibility of the reagents will allow. The test kit can also include other material(s), which may be desirable from a user standpoint, such as a buffer(s), a diluent(s), a standard(s), and/or any other material useful in sample processing, washing, or conducting any other step of the assay.

In certain embodiments, a test kit includes a humanized monoclonal antibody, wherein the humanized monoclonal antibody is specific for the analyte of interest. This component can be used as a positive control in immunoassays according to the invention. If desired, this component can be included in the test kit in multiple concentrations to facilitate the generation of a standard curve to which the signal detected in the test sample can be compared. Alternatively, a standard curve can be generated by preparing dilutions of a single humanized monoclonal antibody solution provided in the kit.

Kits according to the present disclosure can include a solid phase capable of binding autoantibodies present in the test sample, a first antibody that binds to at least one epitope on the analyte of interest, the first antibody bound to the solid phase, a second antibody that binds to at least one epitope on the analyte of interest, and instructions for detecting or quantifying the analyte of interest. In certain embodiments test kits according to the present disclosure may include the solid phase as a material such as a magnetic particle, a bead, a test tube, a microtiter plate, a cuvette, a membrane, a scaffolding molecule, a quartz crystal, a film, a filter paper, a disc or a chip.

Test kits according to the present disclosure can include for example non-human monoclonal antibodies against the analyte of interest, as the first and second antibodies. The kit may also include a detectable label that can be or is conjugated to the second antibody. In certain embodiments, the test kit includes at least one direct label, which may be an enzyme, oligonucleotide, nanoparticle chemiluminophore, fluorophore, fluorescence quencher, chemiluminescence quencher, or biotin. In some embodiments, the direct label is an acridinium compound such as an acridinium-9-carboxamide according to formula I:

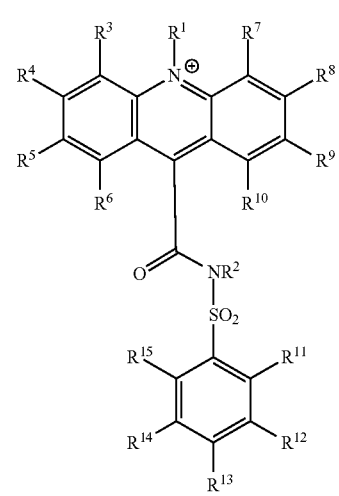

wherein R1 and R2 are each independently selected from the group consisting of: alkyl, alkenyl, alkynyl, aryl or aralkyl, sulfoalkyl, carboxyalkyl and oxoalkyl, and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^\ominus$ is an anion.

Alternatively, the acridinium compound can be an acridinium-9-carboxylate aryl ester having a structure according to formula II:

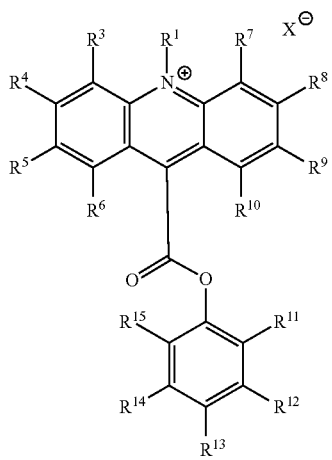

wherein R1 is an alkyl, alkenyl, alkynyl, aryl or aralkyl, sulfoalkyl, carboxyalkyl and oxoalkyl; and wherein R3 through R15 are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and optionally, if present, $X^{\ominus}$ is an anion.

Test kits according to the present disclosure and which include an acridinium compound can also include a basic solution. For example, the basic solution can be a solution having a pH of at least about 10.

In certain embodiments, test kits according to the present disclosure may further include a hydrogen peroxide source, such as a buffer solution, a solution containing hydrogen peroxide, or a hydrogen peroxide generating enzyme. For example, test kits may include an amount of a hydrogen peroxide generating enzymes selected from the following: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, N6-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

In certain embodiments, test kits according to the present disclosure are configured for detection or quantification of one of the following specific analytes of interest cardiac troponin, thyroid stimulating hormone (TSH), beta human chorionic gonadotropin (beta-HCG); myeloperoxidase (MPO), prostate specific antigen (PSA), human B-type natriuretic peptide (BNP), myosin light chain 2, myosin-6 and myosin-7. In such embodiments, the test kits include a first antibody and a second antibody that each bind to an epitope on the selected analyte of interest, i.e. a first antibody and a second antibody and second antibody that each bind to an epitope on one of the following: cardiac troponin, thyroid stimulating hormone (TSH), beta human chorionic gonadotropin (beta-HCG); myeloperoxidase (MPO), prostate specific antigen (PSA), human B-type natriuretic peptide (BNP), myosin light chain 2, myosin-6 and myosin-7.

Test kits according to the present disclosure preferably include instructions for carrying out one or more of the immunoassays of the invention. Instructions included in kits of the present disclosure can be affixed to packaging material or can be included as a package insert. While the instructions are typically written or printed materials they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site that provides the instructions.

D. ADAPTATIONS OF THE METHODS OF THE PRESENT DISCLOSURE

The present disclosure is for example applicable to the jointly owned commercial Abbott Point of Care (i-STAT™) electrochemical immunoassay system which performs sandwich immunoassays for several cardiac markers, including TnI, CKMB and BNP. Immunosensors and ways of operating them in single-use test devices are described in jointly owned Publication Nos. US 20030170881, US 20040018577, US 20050054078, and US 20060160164, each of which is incorporated herein by reference. Additional background on the manufacture of electrochemical and other types of immunosensors is found in jointly owned U.S. Pat. No. 5,063,081 which is also incorporated by reference.

By way of example, and not of limitation, examples of the present disclosures shall now be given.

EXAMPLE 1

Capture of Human IgG on a Magnetic Microparticle Conjugated to an Analyte Specific IgG. (ELN ref: E000777-281)

Microparticles: Carboxylated magnetic microparticles (Polymer Laboratories), MES buffer, EDAC, and anti-troponin-I purified murine IgG's (8E10 and MO6) were added together and the suspension was mixed. The particles were washed with 1% Tween in PBS, then 1% BSA in PBS, then with a diluent (normal goat IgG 0.028 L/L; TRIS 6.05 g/L; EGTA 9.51 g/L; sodium chloride; 5.8 g/L; BSA 10.0 g/L; Brij 35 3.0 g/L; sodium alkyl paraben 1.0 g/L; sarafloxacin hydrochloride 0.01 L/L; Tectronic 1307 10.0 g/L; sucrose 136 g/L), and adjusted to a final concentration of 1% solids.

Human IgG stock solution: Human IgG (Sigma cat#140506 lot 047K7635) was diluted in PBS to give a solution of 50 mg/mL.

Human IgG standard solutions: The human IgG stock solution was serially diluted in PBS to give standard solutions at 25, 12.5, 6.25, 3.13, 1.57, 0.78, 0.39, 0.20, 0.10, 0.05, and 0.025 mg/mL.

Anti-human IgG detection conjugate: An anti-human IgG acridinium-9-carboxamide-labeled conjugate solution (25 ng/mL) was prepared in MOPS buffer (pH 6.3, 0.05% BSA, 1% Triton, 0.1% dextran sulfate).

Figure 3:
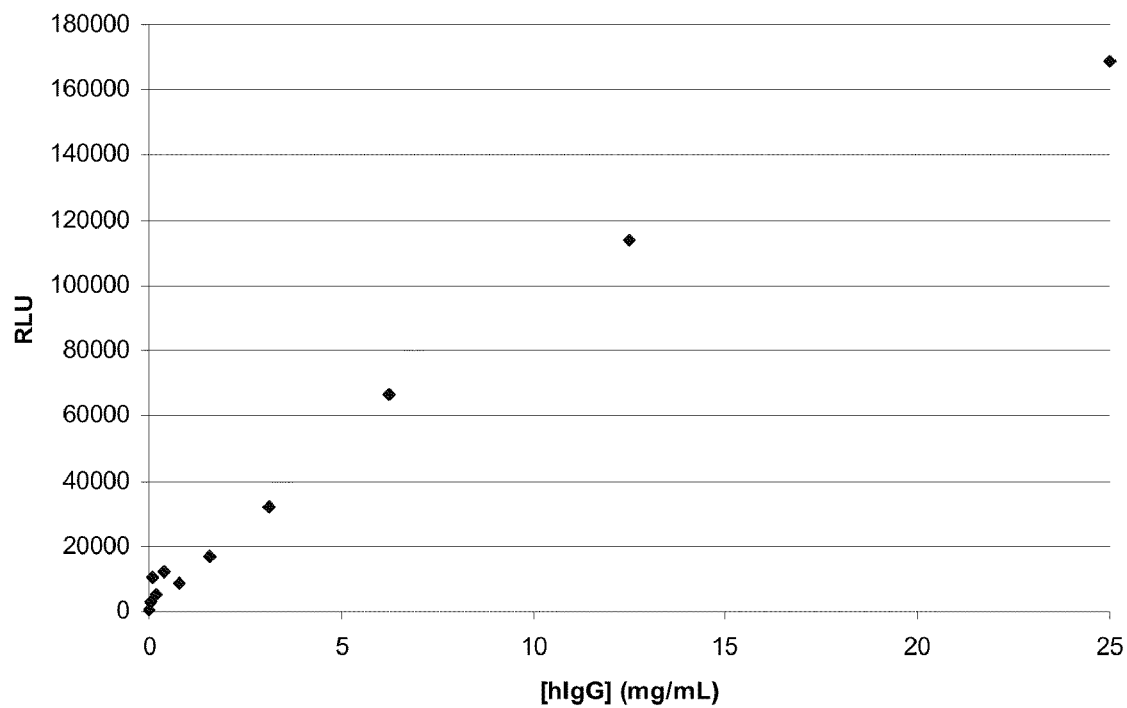
FIG. 3 shows a graph of dose-response of human IgG captured on magnetic microparticles and conjugated to an analyte-specific IgG.

Protocol: The human IgG standard solutions were assayed in duplicate on an ARCHITECT i2000SR using the ARCHITECT stat-Troponin-I protocol, and the microparticles and detection conjugate described above. A point-to-point dose-response curve was constructed by plotting the RLU response obtained from the ARCHITECT assay versus the human IgG concentration tested as shown graphically in FIG. 3.

EXAMPLE 2

Assay for Human IgG in Normal Serum on a Magnetic Microparticle Conjugated to an Analyte Specific IgG. (ELN ref: E000777-281)

Figure 4:
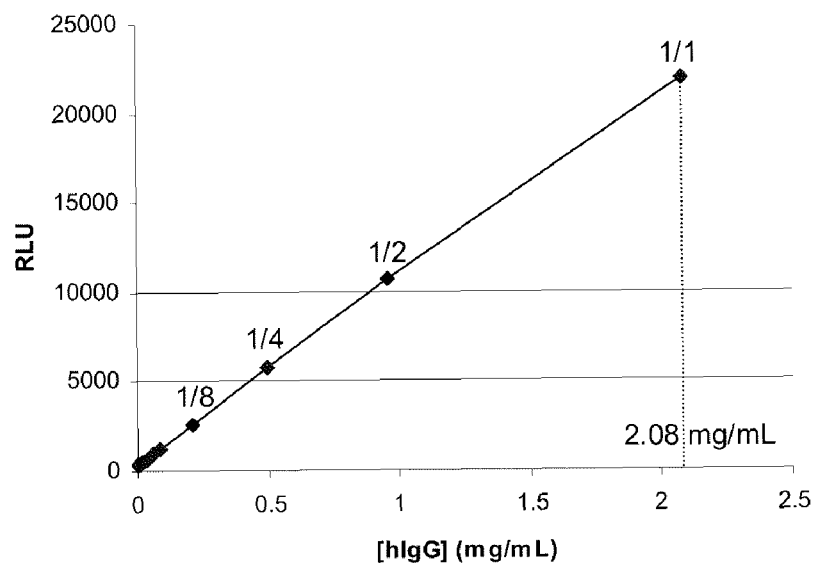
FIG. 4 shows a graph of a serial dilution of IgG from human serum captured on magnetic microparticles and conjugated to an analyte specific IgG.

A normal serum sample was serially diluted in PBS and analyzed using the reagents and protocol from Example 1. The RLU response from the assay was plotted versus the human IgG concentration calculated from the dose-response curve in Example 1 as shown graphically in FIG. 4.

EXAMPLE 3

Effect of Captured Human Anti-Cardiac Troponin-I on a Cardiac Troponin-I Immunoassay. (ELN ref: E000777-278)

Two samples were chosen from a population of normal blood donors screened for anti-cardiac troponin-I autoantibodies (U.S. Ser. No. 11\588073); one was determined to have low-reactivity (LR) in the assay for while the other had high reactivity (HR). Cardiac troponin-I (BiosPacific cat#J34170359) was added to aliquots of each sample at two concentrations to give final cTnI concentrations of 0.25 and 1.5 ng/mL. Each sample was analyzed using the microparticles described in Example 1 and cardiac troponin-I specific detection conjugate and diluents supplied in the ARCHITECT Stat Troponin-I Kit (cat#2K41-30). The sample containing a high level of autoantibodies reactive with cardiac troponin-I showed an increased sensitivity to cardiac troponin-I at both the 0.25 and 1.5 ng/mL level. This is reflected in a 36-37% increase in the B/A and C/A ratios in the HR sample relative to the LR samples, which had only a very low level of autoantibodies reactive with cardiac troponin-I (Table 2).

TABLE 2

Increased sensitivity to cardiac troponin-I in the presence of captured cTnI-autoantibodies

| Sample | | cTnI (ng/mL) | RLU | RLU/A | | % Inc |
|---|---|---|---|---|---|---|
| HR | A | 0 | 327 | — | — | |
| | B | 0.25 | 740 | B/A | 2.3 | 37% |
| | C | 1.5 | 999 | C/A | 3.1 | 36% |
| LR | A | 0 | 402 | — | — | — |
| | B | 0.25 | 662 | B/A | 1.6 | — |
| | C | 1.5 | 906 | C/A | 2.3 | — |

One skilled in the art would readily appreciate that the immunoassays described in the present disclosure are well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the present disclosure disclosed herein without departing from the scope and spirit of the invention.

All patents and publications mentioned in the specification are indicative of the levels of those skilled in the art to which the present disclosure pertains. All patents and publications are herein incorporated by reference to the same extent as if each individual publication was specifically and individually indicated to be incorporated by reference.

The present disclosure illustratively described herein suitably may be practiced in the absence of any element or elements, limitation or limitations which are not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the present disclosure claimed. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. An immunoassay for detecting an analyte of interest in a test sample, the immunoassay comprising the steps of:
    a) contacting a test sample suspected of containing an analyte of interest with a first antibody that binds to at least one epitope on the analyte of interest to form a first antibody-analyte complex, wherein the first antibody is immobilized on a solid phase, and further wherein at least one autoantibody in the test sample binds to at least one epitope on the analyte of interest to form an autoantibody-analyte complex, wherein said autoantibody binds to the solid phase;
    b) contacting said mixture comprising a first antibody-analyte complex and an autoantibody-analyte complex with a second antibody to form a measurable assembly comprising a first antibody-analyte-second antibody complex and an autoantibody-analyte-second antibody complex; wherein the second antibody binds to at least one epitope on the analyte of interest, and further wherein, an optical, electrical, or change-of-state signal of the assembly is measured.

2. The immunoassay of claim 1, wherein the second antibody is conjugated to a detectable label, wherein the detectable label is an enzyme, oligonucleotide, nanoparticle chemiluminophore, fluorophore, fluorescence quencher, chemiluminescence quencher, or biotin.

3. The immunoassay of claims 1 or 2, wherein the optical signal is measured as an analyte concentration dependent change in chemiluminescence, fluorescence, phosphorescence, electrochemiluminescence, ultraviolet absorption, visible absorption, infrared absorption, refraction, surface plasmon resonance.

4. The immunoassay of claims 1 or 2, wherein the electrical signal is measured as an analyte concentration dependent change in current, resistance, potential, mass to charge ratio, or ion count.

5. The immunoassay of claims 1 or 2, wherein the change-of-state signal is measured as an analyte concentration dependent change in size, solubility, mass, or resonance.

6. An immunoassay for detecting an analyte of interest in a test sample, the immunoassay comprising the steps of:

a) contacting a test sample suspected of containing an analyte of interest with a first antibody that binds to at least one epitope on the analyte of interest to form a first antibody-analyte complex, wherein the first antibody is immobilized on a solid phase, and further wherein at least one autoantibody in the test sample binds to at least one epitope on the analyte of interest to form an autoantibody-analyte complex, wherein said autoantibody binds to the solid phase;

b) contacting said mixture comprising a first antibody-analyte complex and an autoantibody-analyte complex, with a second antibody that has been conjugated to a detectable label to form a first antibody-analyte-second antibody complex and an autoantibody-analyte-second antibody complex; wherein the second antibody binds to at least one epitope on the analyte of interest and further wherein, the detectable label is at least one acridinium compound;

c) generating or providing a source of hydrogen peroxide to the mixture of step (b);

d) adding a basic solution to the mixture of step (c) to generate a light signal; and e) measuring the light signal generated by or emitted in step (d) and detecting the analyte of interest in the test sample.

7. The immunoassay of claim 6, wherein the analyte of interest is a cardiac troponin, thyroid stimulating hormone (TSH), beta human chorionic gonadotropin (beta-HCG); myeloperoxidase (MPO), prostate specific antigen (PSA), human B-type natriuretic peptide (BNP), myosin light chain 2, myosin-6 or myosin-7.

8. The immunoassay of claim 6, wherein the test sample is whole blood, serum, plasma.

9. The immunoassay of claim 6, wherein the acridinium compound is an acridinium 9-carboxamide having a structure according to formula I:

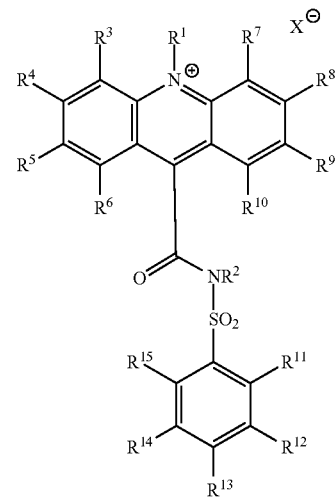

wherein $R^1$ and $R^2$ are each independently selected from the group consisting of:
alkyl, alkenyl, alkynyl, aryl or aralkyl, sulfoalkyl, carboxyalkyl and oxoalkyl, and
wherein $R^3$ through $R^{15}$ are each independently selected from the group consisting of: hydrogen, alkyl, alkenyl, alkynyl, aryl or aralkyl, amino, amido, acyl, alkoxyl, hydroxyl, carboxyl, halogen, halide, nitro, cyano, sulfo, sulfoalkyl, carboxyalkyl and oxoalkyl; and
optionally, if present, $X^\ominus$ is an anion.

10. The immunoassay of claim 6, wherein the acridinium compound is an acridinium-9-carboxylate aryl ester having a structure according to formula II:

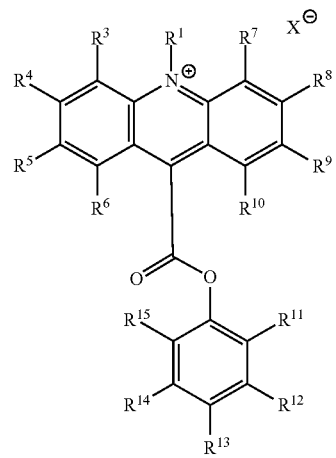

wherein $R^1$ is an alkyl, alkenyl, alkynyl, aryl or aralkyl, sulfoalkyl, carboxyalkyl and oxoalkyl; and wherein $R^3$ through $R^{15}$ are each independently selected from the group consisting of: hydrogen, alkyl, alkenyl, alkynyl, aryl or aralkyl, amino, acyl, alkoxyl, hydroxyl, carboxyl, halogen, halide, nitro, cyano, sulfa, sulfoalkyl, carboxyalkyl and oxoalkyl; and optionally, if present, $X^\ominus$ is an anion.

11. The immunoassay of claim 6, wherein the solid phase is selected from the group consisting of a magnetic particle, bead, test tube, microtiter plate, cuvette, membrane, a scaffolding molecule, quartz crystal, film, filter paper, disc and chip.

12. The immunoassay of claim 6, wherein the first antibody is selected from the group consisting of a polyclonal antibody, a monoclonal antibody, a chimeric antibody, a human antibody, and an affinity maturated antibody.

13. The immunoassay of claim 6, wherein the second antibody is selected from the group consisting of a polyclonal antibody, a monoclonal antibody, a chimeric antibody, a human antibody, and an affinity maturated antibody.

14. The immunoassay of claim 6, wherein the hydrogen peroxide is provided by adding a buffer or a solution containing hydrogen peroxide.

15. The immunoassay of claim 6, wherein the hydrogen peroxide is generated by adding a hydrogen peroxide generating enzyme to the test sample.

16. The immunoassay of claim 15, wherein the hydrogen peroxide generating enzyme is selected from the group consisting of: (R)-6-hydroxynicotine oxidase, (S)-2-hydroxy acid oxidase, (S)-6-hydroxynicotine oxidase, 3-aci-nitropropanoate oxidase, 3-hydroxyanthranilate oxidase, 4-hydroxymandelate oxidase, 6-hydroxynicotinate dehydrogenase, abscisic-aldehyde oxidase, acyl-CoA oxidase, alcohol oxidase, aldehyde oxidase, amine oxidase, amine oxidase (copper-containing), amine oxidase (flavin-containing), aryl-alcohol oxidase, aryl-aldehyde oxidase, catechol oxidase, cholesterol oxidase, choline oxidase, columbamine oxidase, cyclohexylamine oxidase, cytochrome c oxidase, D-amino-acid oxidase, D-arabinono-1,4-lactone oxidase, D-arabinono-1,4-lactone oxidase, D-aspartate oxidase, D-glutamate oxidase, D-glutamate(D-aspartate) oxidase, dihydrobenzophenanthridine oxidase, dihydroorotate oxidase, dihydrouracil oxidase, dimethylglycine oxidase, D-mannitol oxidase, ecdysone oxidase, ethanolamine oxidase, galactose oxidase, glucose oxidase, glutathione oxidase, glycerol-3-phosphate oxidase, glycine oxidase, glyoxylate oxidase, hexose oxidase, hydroxyphytanate oxidase, indole-3-acetaldehyde oxidase, lactic acid oxidase, L-amino-acid oxidase, L-aspartate oxidase, L-galactonolactone oxidase, L-glutamate oxidase, L-gulonolactone oxidase, L-lysine 6-oxidase, L-lysine oxidase, long-chain-alcohol oxidase, L-pipecolate oxidase, L-sorbose oxidase, malate oxidase, methanethiol oxidase, monoamino acid oxidase, $N^6$-methyl-lysine oxidase, N-acylhexosamine oxidase, NAD(P)H oxidase, nitroalkane oxidase, N-methyl-L-amino-acid oxidase, nucleoside oxidase, oxalate oxidase, polyamine oxidase, polyphenol oxidase, polyvinyl-alcohol oxidase, prenylcysteine oxidase, protein-lysine 6-oxidase, putrescine oxidase, pyranose oxidase, pyridoxal 5'-phosphate synthase, pyridoxine 4-oxidase, pyrroloquinoline-quinone synthase, pyruvate oxidase, pyruvate oxidase (CoA-acetylating), reticuline oxidase, retinal oxidase, rifamycin-B oxidase, sarcosine oxidase, secondary-alcohol oxidase, sulfite oxidase, superoxide dismutase, superoxide reductase, tetrahydroberberine oxidase, thiamine oxidase, tryptophan α,β-oxidase, urate oxidase (uricase, uric acid oxidase), vanillyl-alcohol oxidase, xanthine oxidase, xylitol oxidase and combinations thereof.

17. The immunoassay of claim 6, wherein the basic solution is a solution having a pH of at least about 10.

18. The immunoassay of claim 6, further comprising the step of quantifying the amount of the analyte of interest in the test sample by relating the amount of light signal in step (e) to the amount of the analyte of interest in the test sample either by use of a standard curve for the analyte of interest or by comparison to a reference standard.

19. The is immunoassay of claim 6, wherein the immunoassay is adapted for use in an automated system or semi-automated system.

\* \* \* \* \*

UNITED STATES PATENT AND TRADEMARK OFFICE
CERTIFICATE OF CORRECTION

| | | |
|---|---|---|
| PATENT NO. | : 8,183,002 B2 | Page 1 of 2 |
| APPLICATION NO. | : 12/630697 | |
| DATED | : May 22, 2012 | |
| INVENTOR(S) | : Adamczyk et al. | |

It is certified that error appears in the above-identified patent and that said Letters Patent is hereby corrected as shown below:

In the Claims:

Column 32, line 63, claim 1: "a first antibody-analyte complex" to read as --the first antibody-analyte complex--

Column 32, line 64, claim 1: "an autoantibody-analyte complex" to read as --the autoantibody-analyte complex--

Column 33, line 01, claim 1: "complex; wherein" to read as --complex, wherein--

Column 33, line 11, claim 3: "claims 1 or 2," to read as --claim 1 or 2,--

Column 33, line 16, claim 3: "refraction, surface plasmon resonance." to read as --refraction, or surface plasmon resonance.--

Column 33, line 18, claim 4: "claims 1 or 2," to read as --claim 1 or 2,--

Column 33, line 23, claim 5: "claims 1 or 2," to read as --claim 1 or 2,--

Column 33, line 38, claim 6: "a first antibody-analyte complex" to read as --the first antibody-analyte complex--

Column 33, line 39, claim 6: "an autoantibody-analyte complex," to read as --the autoantibody-analyte complex,--

Column 33, line 43, claim 6: "complex; wherein" to read as --complex, wherein--

Column 33, line 59, claim 7: "(beta-HCG);" to read as --(beta-HCG),--

Signed and Sealed this
Fifteenth Day of July, 2014

Michelle K. Lee
*Deputy Director of the United States Patent and Trademark Office*

CERTIFICATE OF CORRECTION (continued)
U.S. Pat. No. 8,183,002 B2

Column 33, line 64, claim 8: "serum, plasma." to read as --serum or plasma.--

Column 33, line 66, claim 9: "acridinium 9-carboxamide" to read as --acridinium-9-carboxamide--

Column 34, line 59, claim 10: "consisting of" to read as --consisting of:--

Column 34, line 60, claim 10: "amino, acyl," to read as --amino, amido, acyl,--

Column 34, line 61, claim 10: "sulfa," to read as --sulfo,--

Column 35, line 27, claim 16: "D-arabinono-1,4-lactone oxidase, D-arabinono-1,4-lactone oxidase," to read as --D-arabinono-1,4-lactone oxidase,--

Column 36, line 31, claim 19: "The is" to read as --The--